US010519239B2

(12) United States Patent
Chatenet et al.

(10) Patent No.: US 10,519,239 B2
(45) Date of Patent: Dec. 31, 2019

(54) INHIBITORS OF PROTOTYPIC GALECTIN DIMERIZATION AND USES THEREOF

(71) Applicant: INSTITUT NATIONAL DE LA RECHERCHE SCIENTIFIQUE, Québec, Québec (CA)

(72) Inventors: David Chatenet, Lorraine (CA); Nicolas Doucet, Laval (CA); Yves St-Pierre, Laval (CA); Maria-Claudia Vladoiu, Laval (CA)

(73) Assignee: INSTITUT NATIONAL DE LA RECHERCHE SCIENTIFIQUE, Quebec (CA)

( * ) Notice: Subject to any disclaimer, the term of this patent is extended or adjusted under 35 U.S.C. 154(b) by 0 days.

(21) Appl. No.: 15/576,609

(22) PCT Filed: May 25, 2016

(86) PCT No.: PCT/CA2016/050587
§ 371 (c)(1),
(2) Date: Nov. 22, 2017

(87) PCT Pub. No.: WO2016/187712
PCT Pub. Date: Dec. 1, 2016

(65) Prior Publication Data
US 2018/0155432 A1 Jun. 7, 2018

Related U.S. Application Data

(60) Provisional application No. 62/167,512, filed on May 28, 2015.

(51) Int. Cl.
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/00 | (2006.01) |
| A61P 35/00 | (2006.01) |
| A61K 38/10 | (2006.01) |
| A61K 38/16 | (2006.01) |
| A61K 38/08 | (2019.01) |
| C07K 16/28 | (2006.01) |
| C07K 7/06 | (2006.01) |
| C07K 7/08 | (2006.01) |
| A61K 38/17 | (2006.01) |
| C07K 14/47 | (2006.01) |
| A61K 39/395 | (2006.01) |
| G01N 33/531 | (2006.01) |

(52) U.S. Cl.
CPC .......... *C07K 16/2851* (2013.01); *A61K 38/08* (2013.01); *A61K 38/10* (2013.01); *A61K 38/17* (2013.01); *A61K 39/39533* (2013.01); *A61P 35/00* (2018.01); *C07K 7/06* (2013.01); *C07K 7/08* (2013.01); *C07K 14/4702* (2013.01); *A61K 38/00* (2013.01); *C07K 2317/34* (2013.01); *G01N 33/531* (2013.01); *G01N 2500/04* (2013.01); *G01N 2800/7028* (2013.01)

(58) Field of Classification Search
None
See application file for complete search history.

(56) References Cited

U.S. PATENT DOCUMENTS

2012/0328568 A1* 12/2012 Cummings .......... A61K 38/178
424/85.7

OTHER PUBLICATIONS

Madsen et al., J. Biol. Chem. 270:5823-5829 (1996) (Year: 1996).*
Kaur et al., Asian Pac. J. Cancer Prev. 17:455-461 (2016) (Year: 2016).*
Akahani, S., et al., Galectin-3: a novel antiapoptotic molecule with a functional BH1 (NWGR) domain of Bcl-2 family. Cancer Res, 1997. 57(23): p. 5272-6.
Barondes, S.H., et al., Galectins: a family of animal beta-galactoside-binding lectins. Cell, 1994. 76(4): p. 597-8.
Barondes, S.H., et al., Galectins. Structure and function of a large family of animal lectins. J Biol Chem, 1994. 269(33): p. 20807-10.
Boscher, C., J.W. Dennis, and I.R. Nabi, Glycosylation, galectins and cellular signaling. Curr Opin Cell Biol, 2011. 23(4): p. 383-92.
Fred Brewer, C., Binding and cross-linking properties of galectins. Biochim Biophys Acta, 2002. 1572(2-3): p. 255-62.
Brkovic, A., et al., Functional and binding characterizations of urotensin II-related peptides in human and rat urotensin II-receptor assay. J Pharmacol Exp Ther, 2003. 306(3): p. 1200-9.
Cooper, D.N., Galectinomics: finding themes in complexity. Biochim Biophys Acta, 2002. 1572(2-3): p. 209-31.
Dings, R.P., et al., Antitumor agent calixarene 0118 targets human galectin-1 as an allosteric inhibitor of carbohydrate binding. J Med Chem, 2012. 55(11): p. 5121-9.

(Continued)

Primary Examiner — James H Alstrum-Acevedo
Assistant Examiner — Thea D'Ambrosio
(74) Attorney, Agent, or Firm — Myers Bigel, P.A.

(57) ABSTRACT

Agents that inhibit the dimerization of a prototypic galectin such as galectin-7 are described. These agents, for example antibodies and peptides, bind to a domain corresponding to residues 13-25, 86-108 and/or 129-135 of human galectin-7. The use of such agents to inhibit a biological, physiological and/or pathological process that involves prototypic galectin dimerization, for example for the inhibition of galectin-7-mediated apoptosis and the treatment of galectin-7-expressing cancers, is also described.

19 Claims, 12 Drawing Sheets
Specification includes a Sequence Listing.

(56) References Cited

OTHER PUBLICATIONS

Doan, N.D., et al., Design and characterization of novel cell-penetrating peptides from pituitary adenylate cyclase-activating polypeptide. J Control Release, 2012. 163(2): p. 256-65.

Ermakova, E., et al., Lactose binding to human galectin-7 (p53-induced gene 1) induces long-range effects through the protein resulting in increased dimer stability and evidence for positive cooperativity. Glycobiology, 2013. 23(5): p. 508-23.

Fukata, Y., et al., Direct cytocidal effect of galectin-9 localized on collagen matrices on human immune cell lines. Biochim Biophys Acta, 2014. 1840(6): p. 1892-901.

Garner, O.B. and L.G. Baum, Galectin-glycan lattices regulate cell-surface glycoprotein organization and signalling. Biochem Soc Trans, 2008. 36(Pt 6): p. 1472-7.

George, S.R., et al., A transmembrane domain-derived peptide inhibits D1 dopamine receptor function without affecting receptor oligomerization. J Biol Chem, 1998. 273(46): p. 30244-8.

Giudicelli, V., et al., Is human galectin-1 activity modulated by monomer/dimer equilibrium? Glycobiology, 1997. 7(3): p. viii-x.

Giudici, A.M., et al., Detergent-labile, supramolecular assemblies of KcsA: relative abundance and interactions involved. Biochim Biophys Acta, 2013. 1828(2): p. 193-200.

Hanahan, D. and R.A. Weinberg, Hallmarks of cancer: the next generation. Cell. 2011. 144(5): p. 646-74.

Hebert, T.E., et al., A peptide derived from a beta2-adrenergic receptor transmembrane domain inhibits both receptor dimerization and activation. J Biol Chem, 1996. 271(27): p. 16384-92.

Henrick, K., et al., Evidence for subsites in the galectins involved in sugar binding at the nonreducing end of the central galactose of oligosaccharide ligands: sequence analysis, homology modeling and mutagenesis studies of hamster galectin-3. Glycobiology, 1998. 8(1): p. 45-57.

Hoang, T., M.D. Smith, and M. Jelokhani-Niaraki, Expression, folding, and proton transport activity of human uncoupling protein-1 (UCP1) in lipid membranes: evidence for associated functional forms. J Biol Chem, 2013. 288(51): p. 36244-58.

Inohara, H. and A. Raz, Effects of natural complex carbohydrate (citrus pectin) on murine melanoma cell properties related to galectin-3 functions. Glycoconj J, 1994. 11(6): p. 527-32.

Ito, K., et al., Galectin-1 as a potent target for cancer therapy: role in the tumor microenvironment. Cancer Metastasis Rev, 2012. 31(3-4): p. 763-78.

Jahnel, R., et al., Biochemical characterization of the vanilloid receptor 1 expressed in a dorsal root ganglia derived cell line. Eur J Biochem, 2001. 268(21): p. 5489-96.

Klemm, F. and J.A. Joyce, Microenvironmental regulation of therapeutic response in cancer. Trends Cell Biol, 2015. 25(4): p. 198-213.

Klodmann, J., D. Lewejohann, and H.P. Braun, Low-SDS Blue native PAGE. Proteomics, 2011. 11(9): p. 1834-9.

Kubak, B.M. and W.W. Yotis, *Staphylococcus aureus* adenosine triphosphatase: Inhibitor sensitivity and release from membrane. J Bacteriol, 1981. 146(1): p. 385-90.

Labrie, M., et al., Expression and functions of galectin-7 in ovarian cancer. Onoctarget, 2014. 5(17): p. 7705-21.

Leonidas, D.D., et al., Structural basis for the recognition of carbohydrates by human galectin-7. Biochemistry, 1998. 37(40): p. 13930-40.

Levi, G. and V.I. Teichberg, Isolation and physicochemical characterization of electrolectin, a beta-D-galactoside binding lectin from the electric organ of Electrophorus electricus. J Biol Chem, 1981. 256(11): p. 5735-40.

Lin, C.L., Y.T. Huang, and J.D, Richter, Transient CPEB dimerization and translational control. RNA, 2012. 18(5): p. 1050-61.

Liu, F.T. and G.A. Rabinovich, Galectins as modulators of tumour progression. Nat Rev Cancer, 2005. 5(1): p. 29-41.

Masuyer, G. et al. Inhibition mechanism of human galectin-7 by a novel galactose-benzylphosphate inhibitor. FEBS Journal 279 (2012) 193-202.

Nangia-Makker, P., et al., Inhibition of human cancer cell growth and metastasis in nude mice by oral intake of modified citrus pectin. J Natl Cancer Inst, 2002. 94(24): p. 1854-62.

Norambuena, A., et al., Galectin-8 induces apoptosis in Jurkat T cells by phosphatidic acid-mediated ERK1/2 activation supported by protein kinase A down-regulation. J Biol Chem, 2009. 284(19): p. 12670-9.

Oliver, D.B., et al., Azide-resistant mutants of *Escherichia coli* alter the SecA protein, an azide-sensitive component of the protein export machinery. Proc Natl Acad Sci USA, 1990. 87(21): p. 8227-31.

Paz, A., et al., Galectin-1 binds oncogenic H-Ras to mediate Ras membrane anchorage and cell transformation. Oncogene, 2001. 20(51): p. 7486-93.

PCT International Search Report and Written Opinion in respect of PCT application No. PCT/CA2016/050587, dated Aug. 30, 2016.

Perillo, N.L., et al., Apoptosis of T cells mediated by galectin-1. Nature, 1995. 378(6558): p. 736-9.

Pienta, K.J., et al., Inhibition of spontaneous metastasis in a rat prostate cancer model by oral administration of modified citrus pectin. J Natl Cancer Inst, 1995. 87(5): p. 348-53.

Quail, D.F. and J.A. Joyce, Microenvironmental regulation of tumor progression and metastasis. Nat Med, 2013. 19(11): p. 1423-37.

Rabinovich, G.A., et al., Functions of cell surface galectin-glycoprotein lattices. Curr Opin Struct Biol, 2007. 17(5): p. 513-20.

Radosavijevic, G., et al., The roles of Galectin-3 in autoimmunity and tumor progression. Immunol Res, 2012. 52(1-2): p. 100-10.

Shimura, T., et al., Implication of galectin-3 in Wnt signaling. Cancer Res, 2005. 65(9): p. 3535-7.

Stannard, K.A., et al., Galectin inhibitory disaccharides promote tumour immunity in a breast cancer model. Cancer Lett, 2010. 299(2): p. 95-110.

Stillman, B.N., et al., Galectin-3 and galectin-1 bind distinct cell surface glycoprotein receptors to induce T cell death. J Immunol, 2006. 176(2): p. 778-89.

Than, N.G. et al., A primate subfamily of galectins expressed at the maternal-fetal interface that promote immune cell death, Proc Natl Acad Sci USA (2009) 106(24), 9731-36.

Than, N.G. et al., Galectins: guardians of eutherian pregnancy at the maternalfetal interfaceTrends in Endocrinology and Metabolism (2012), 23(1), 23-31.

Tribulatti, M.V., et al., Gatectin-8 induces apoptosis in the CD4(high)CD8(high) thymocyte subpopulation, Glycobiology, 2007. 17(12): p. 1404-12.

Vasta, G.R., Roles of galectins in infection. Nat Rev Microbiol, 2009. 7(6): p. 424-38.

Villeneuve, C., et al., Mitochondrial proteomic approach reveals galectin-7 as a novel BCL-2 binding protein in human cells. Mol Biol Cell, 2011. 22(7): p. 999-1013.

Vladoiu, M.C., et al. Design of a peptidic inhibitor that targets the dimer interface of a prototypic galectin. Oncotarget (2015), vol. 6, No. 38, p. 40970-80.

Wang, W., et al., Tumor-released Galectin-3, a soluble inhibitory ligand of human NKp30, plays an important role in tumor escape from NK cell attack. J Biol Chem, 2014. 289(48): p. 33311-9.

Wang, D. and R.N. Dubois, Eicosanoids and cancer. Nat Rev Cancer, 2010. 10(3): p. 181-93.

Xue, J., et al., Regulation of galectin-3-induced apoptosis of Jurkat cells by both O-glycans and N-glycans on CD45. FEBS Lett, 2013. 587(24): p. 3986-94.

Yang, R.Y., G.A. Rabinovich, and F.T. Liu, Galectins: structure, function and therapeutic potential. Expert Rev Mol Med, 2008. 10: p. e17.

Notification of Transmittal of the International Search Report and the Written Opinion of the International Searching Authority, or the Declaration corresponding to International Application No. PCT/CA2016/050587 dated Aug. 30, 2016.

Leonidas et al. "Structural Basis for the Recognition of Carbohydrates by Human Galectin-7+,+", Biochemistry 37(40):13930-13940 (1998).

Mayo "From Carbohydrate to Peptidomimetic Inhibitors of Galectins", ACS Symposium Series, American Chemical Society/Oxford University Press 1115:61-77 (2012).

(56) References Cited

OTHER PUBLICATIONS

Zou et al. "Peptides specific to the galectin-3 carbohydrate recognition domain inhibit metastasis-associated cancer cell adhesion", Carcinogenesis 26(2):309-318 (2005).
Extended European Search Report corresponding to European Application No. 16798994.6 dated Sep. 14, 2018.

\* cited by examiner

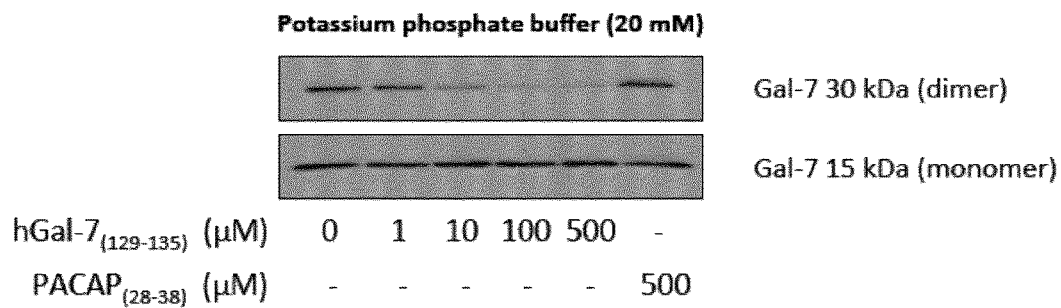
FIG. 2A
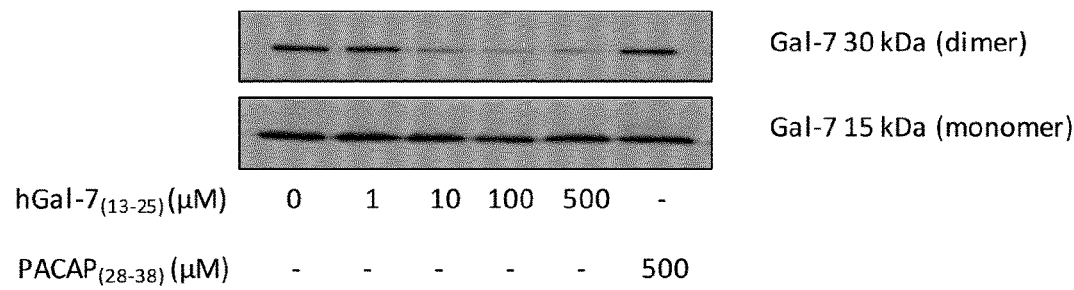
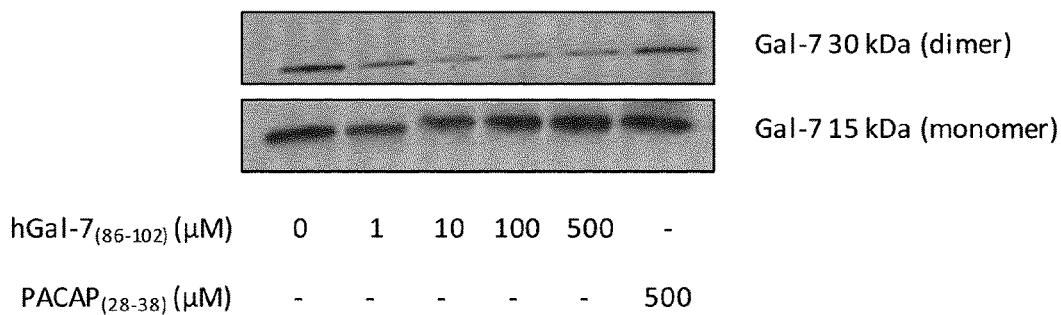
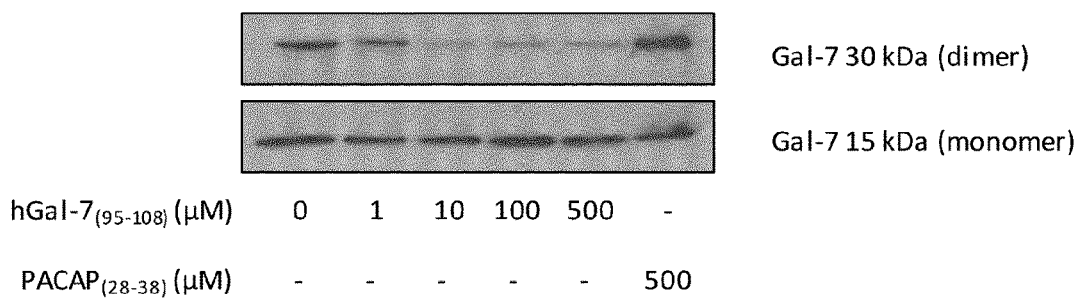
FIG. 2B

```
  1 msnvphkssl pegirpgtvl rirglvppna srfhvnllcg eeqgsdaalh fnprldtsev
 61 vfnskeqgsw greergpgvp fqrgqpfevl iiasddgfka vvgdaqyhhf rhrlplarvr
121 lvevggdvql dsvrif
```

FIG. 10A

```
  1 acggctgccc aacccggtcc cagccatgtc caacgtcccc acaagtcct cactgcccga
 61 gggcatccgc cctggcacgg tgctgagaat tcgcggcttg gttcctccca atgccagcag
121 gttccatgta aacctgctgt gcggggagga gcagggctcc gatgccgcgc tgcatttcaa
181 cccccggctg gacacgtcgg aggtggtctt caacagcaag gagcaaggct cctgggccg
241 cgaggagcgc gggccgggcg ttcctttcca gcgcgggcag cccttcgagg tgctcatcat
301 cgcgtcagac gacggcttca aggccgtggt tggggacgcc cagtaccacc acttccgcca
361 ccgcctgccg ctggcgcgcg tgcgcctggt ggaggtgggc ggggacgtgc agctggactc
421 cgtgaggatc ttctgagcag aagcccaggc gggcccgggg ccttggctgg caaataaagc
481 gttagcccgc agcgaaaaaa aaaaaaaaaa aaaaa
```

FIG. 10B

```
CLUSTAL 2.1 multiple sequence alignment
                                                      13-25
                                     hGal
gi|7019497|ref|NP_037400.1|   13   MSSLPVPYKLPVSLSVGSCVIIKGTPIHSFINDPQLQVDFYTDMD-EDSD 49
gi|9910348|ref|NP_064514.1|   14   MSSLPVPYTLPVSLPVGSCVIITGTPILTFVKDPQLEVNFYTGMD-EDSD 49
gi|20357559|ref|NP_001819.2| 10   MSLLPVPYTEAASLSTGSTVTIKGRPLACFLNEPYLQVDFHTEMK-EESD 49
gi|4504985|ref|NP_002298.1|   7   MSNVPHKSSLPEGIRPGTVLRIRG---LVPPNASRFHVNLLCGEE-QGSD 46
gi|4504981|ref|NP_002296.1|   1   --MACGLVASNLNLKPGECLRVRG---EVAPDAKSFVLNLGKDSNNLCLH 45
gi|5729903|ref|NP_006489.1|   2   --MTGELEVKNMDMKPGSTLKITG---SIADGTDGFVINLGQGTDKLNLH 45
                                     .:  *  :: *         : :::    .

82-108
gi|7019497|ref|NP_037400.1|   13   IAFRFRVHFG-NHVVMNRREFGIWMLEETTDYVPFEDGKQFELCIYVHYN 98
gi|9910348|ref|NP_064514.1|   14   IAFQFRLHFG-HPAIMNSCVFGIWRYEEKCYYLPFEDGKPFELCIYVRHK 98
gi|20357559|ref|NP_001819.2| 10   IVFHFQVCFG-RRVVMNSREYGAWKQQVESKNMPFQDGQEFELSISVLPD 98
gi|4504985|ref|NP_002298.1|   7   AALHFNPRLDTSEVVFNSKEQGSWGREERGPGVPFQRGQPFEVLIIASDD 96
gi|4504981|ref|NP_002296.1|   1   FNPRFNAHGDANTIVCNSKDGGAWGTEQREAVFPFQPGSVAEVCITFDQA 95
gi|5729903|ref|NP_006489.1|   2   FNPRFSES----TIVCNSLDGSNWGQEQREDHLCFSPGSEVKFTVTFESD 91
                                    :*       : *  .  *  . *.*. :. :

129-135
gi|7019497|ref|NP_037400.1|   13   EYEIKVNGIRIYGFVHRIPPSFVKMVQSRDISLTSVCVCN--- 139
gi|9910348|ref|NP_064514.1|   14   EYKVMVNGQRIYNFAHRFPPASVKMLQVFRDISLTRVLISD--- 139
gi|20357559|ref|NP_001819.2| 10   KYQVMVNGQSSYTFDHRIKPEAVKMVQVWRDISLTKFNVSYLKR 142
gi|4504985|ref|NP_002298.1|   7   GFKAVVGDAQYHHFRHRLPLARVRLVEVGGDVQLDSVRIF---- 136
gi|4504981|ref|NP_002296.1|   1   NLTVKLPDGYEFKFPNRLNLEAINYMAADGDFKIKCVAFD---- 135
gi|5729903|ref|NP_006489.1|   2   KFKVKLPDGHELTFPNRLGHSHLSYLSVRGGFNMSSFKLKE--- 132
                                   :.       * :*:     :  :.    ...:  . .
```

FIG. 11

Gal-7 Antibody

Gal-7/Bcl-2 complex 42kDa

Gal-7 30 kDa (dimer)

Gal-7 15 kDa (monomer)

Gal-7 (0.1 µM)   +     +     +     +     +
Bcl2 (µM)        -    0.05  0.1   0.5    1

Bcl-2 Antibody

Gal-7/Bcl-2 complex 42kDa

Bcl-2 27 kDa

Gal-7 (0.1 µM)   +     +     +     +     +
Bcl2 (µM)        -    0.05  0.1   0.5    1

Gal-7 Antibody

Gal-7/Bcl-2 complex 42kDa
Gal-7 30 kDa (dimer)

Gal-7 15 kDa (monomer)

Gal-7 (0.5 µM)          +   +   +   +   +   +
Bcl2 (0.5 µM)           -   +   +   +   +   +
hGal-7$_{(129-135)}$ (µM)  -   -   1  10 100 500

SEQUENCE LISTING

<160> NUMBER OF SEQ ID NOS: 19

<210> SEQ ID NO 1
<211> LENGTH: 7
<212> TYPE: PRT
<213> ORGANISM: Homo sapiens

<400> SEQUENCE: 1

Leu Asp Ser Val Arg Ile Phe
1               5

<210> SEQ ID NO 2
<211> LENGTH: 7
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: AMIDATION

<400> SEQUENCE: 2

Leu Asp Ser Val Arg Ile Phe
1               5

<210> SEQ ID NO 3
<211> LENGTH: 13
<212> TYPE: PRT
<213> ORGANISM: Homo sapiens

<400> SEQUENCE: 3

Ile Arg Pro Gly Thr Val Leu Arg Ile Arg Gly Leu Val
1               5                   10

<210> SEQ ID NO 4
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: AMIDATION

<400> SEQUENCE: 4

Ile Arg Pro Gly Thr Val Leu Arg Ile Arg Gly Leu Val
1               5                   10

<210> SEQ ID NO 5
<211> LENGTH: 14
<212> TYPE: PRT
<213> ORGANISM: Homo sapiens

<400> SEQUENCE: 5

Asp Gly Phe Lys Ala Val Val Gly Asp Ala Gln Tyr His His
1               5                   10

<210> SEQ ID NO 6
<211> LENGTH: 14
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: AMIDATION

<400> SEQUENCE: 6

Asp Gly Phe Lys Ala Val Val Gly Asp Ala Gln Tyr His His
1               5                   10

```
<210> SEQ ID NO 7
<211> LENGTH: 17
<212> TYPE: PRT
<213> ORGANISM: Homo sapiens

<400> SEQUENCE: 7

Phe Glu Val Leu Ile Ile Ala Ser Asp Asp Gly Phe Lys Ala Val Val
1               5                   10                  15

Gly

<210> SEQ ID NO 8
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 8

Phe Glu Val Leu Ile Ile Ala Ser Asp Asp Gly Phe Lys Ala Val Val
1               5                   10                  15

Gly

<210> SEQ ID NO 9
<211> LENGTH: 7
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: AMIDATION

<400> SEQUENCE: 9

Leu Ala Ser Val Arg Ile Phe
1               5

<210> SEQ ID NO 10
<211> LENGTH: 7
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: AMIDATION

<400> SEQUENCE: 10

Leu Asp Ala Val Arg Ile Phe
1               5

<210> SEQ ID NO 11
<211> LENGTH: 7
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: AMIDATION

<400> SEQUENCE: 11

Leu Asp Ser Val Ala Ile Phe
1               5

<210> SEQ ID NO 12
<211> LENGTH: 7
```

```
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: AMIDATION

<400> SEQUENCE: 12

Leu Asp Ser Val Arg Ile Ala
1               5

<210> SEQ ID NO 13
<211> LENGTH: 515
<212> TYPE: DNA
<213> ORGANISM: Homo sapiens
<220> FEATURE:
<221> NAME/KEY: CDS
<222> LOCATION: (26)..(436)

<400> SEQUENCE: 13
acggctgccc aacccggtcc cagcc atg tcc aac gtc ccc cac aag tcc tca      52
                            Met Ser Asn Val Pro His Lys Ser Ser
                            1               5 ctg ccc gag ggc atc cgc cct ggc acg gtg ctg aga att cgc ggc ttg     100
Leu Pro Glu Gly Ile Arg Pro Gly Thr Val Leu Arg Ile Arg Gly Leu
 10              15                  20                  25 gtt cct ccc aat gcc agc agg ttc cat gta aac ctg ctg tgc ggg gag     148
Val Pro Pro Asn Ala Ser Arg Phe His Val Asn Leu Leu Cys Gly Glu
                30                  35                  40 gag cag ggc tcc gat gcc gcg ctg cat ttc aac ccc cgg ctg gac acg     196
Glu Gln Gly Ser Asp Ala Ala Leu His Phe Asn Pro Arg Leu Asp Thr
                45                  50                  55 tcg gag gtg gtc ttc aac agc aag gag caa ggc tcc tgg ggc cgc gag     244
Ser Glu Val Val Phe Asn Ser Lys Glu Gln Gly Ser Trp Gly Arg Glu
                60                  65                  70 gag cgc ggg ccg ggc gtt cct ttc cag cgc ggg cag ccc ttc gag gtg     292
Glu Arg Gly Pro Gly Val Pro Phe Gln Arg Gly Gln Pro Phe Glu Val
    75                  80                  85 ctc atc atc gcg tca gac gac ggc ttc aag gcc gtg gtt ggg gac gcc     340
Leu Ile Ile Ala Ser Asp Asp Gly Phe Lys Ala Val Val Gly Asp Ala
90                  95                  100                 105 cag tac cac cac ttc cgc cac cgc ctg ccg ctg gcg cgc gtg cgc ctg     388
Gln Tyr His His Phe Arg His Arg Leu Pro Leu Ala Arg Val Arg Leu
                110                 115                 120 gtg gag gtg ggc ggg gac gtg cag ctg gac tcc gtg agg atc ttc tga     436
Val Glu Val Gly Gly Asp Val Gln Leu Asp Ser Val Arg Ile Phe
                125                 130                 135 gcagaagccc aggcgggccc ggggccttgg ctggcaaata aagcgttagc ccgcagcgaa    496
aaaaaaaaaa aaaaaaaa                                                  515

<210> SEQ ID NO 14
<211> LENGTH: 136
<212> TYPE: PRT
<213> ORGANISM: Homo sapiens

<400> SEQUENCE: 14

Met Ser Asn Val Pro His Lys Ser Ser Leu Pro Glu Gly Ile Arg Pro
1               5                   10                  15

Gly Thr Val Leu Arg Ile Arg Gly Leu Val Pro Pro Asn Ala Ser Arg
                20                  25                  30

Phe His Val Asn Leu Leu Cys Gly Glu Glu Gln Gly Ser Asp Ala Ala
            35                  40                  45
```

Leu His Phe Asn Pro Arg Leu Asp Thr Ser Glu Val Val Phe Asn Ser
            50                  55                  60

Lys Glu Gln Gly Ser Trp Gly Arg Glu Glu Arg Gly Pro Gly Val Pro
 65                  70                  75                  80

Phe Gln Arg Gly Gln Pro Phe Glu Val Leu Ile Ile Ala Ser Asp Asp
                    85                  90                  95

Gly Phe Lys Ala Val Val Gly Asp Ala Gln Tyr His His Phe Arg His
                100                 105                 110

Arg Leu Pro Leu Ala Arg Val Arg Leu Val Glu Val Gly Gly Asp Val
            115                 120                 125

Gln Leu Asp Ser Val Arg Ile Phe
        130                 135

<210> SEQ ID NO 15
<211> LENGTH: 135
<212> TYPE: PRT
<213> ORGANISM: Homo sapiens

<400> SEQUENCE: 15

Met Ala Cys Gly Leu Val Ala Ser Asn Leu Asn Leu Lys Pro Gly Glu
 1                5                  10                  15

Cys Leu Arg Val Arg Gly Glu Val Ala Pro Asp Ala Lys Ser Phe Val
                20                  25                  30

Leu Asn Leu Gly Lys Asp Ser Asn Asn Leu Cys Leu His Phe Asn Pro
            35                  40                  45

Arg Phe Asn Ala His Gly Asp Ala Asn Thr Ile Val Cys Asn Ser Lys
 50                  55                  60

Asp Gly Gly Ala Trp Gly Thr Glu Gln Arg Glu Ala Val Phe Pro Phe
 65                  70                  75                  80

Gln Pro Gly Ser Val Ala Glu Val Cys Ile Thr Phe Asp Gln Ala Asn
                    85                  90                  95

Leu Thr Val Lys Leu Pro Asp Gly Tyr Glu Phe Lys Phe Pro Asn Arg
                100                 105                 110

Leu Asn Leu Glu Ala Ile Asn Tyr Met Ala Ala Asp Gly Asp Phe Lys
            115                 120                 125

Ile Lys Cys Val Ala Phe Asp
        130                 135

<210> SEQ ID NO 16
<211> LENGTH: 132
<212> TYPE: PRT
<213> ORGANISM: Homo sapiens

<400> SEQUENCE: 16

Met Thr Gly Glu Leu Glu Val Lys Asn Met Asp Met Lys Pro Gly Ser
 1                5                  10                  15

Thr Leu Lys Ile Thr Gly Ser Ile Ala Asp Gly Thr Asp Gly Phe Val
                20                  25                  30

Ile Asn Leu Gly Gln Gly Thr Asp Lys Leu Asn Leu His Phe Asn Pro
            35                  40                  45

Arg Phe Ser Glu Ser Thr Ile Val Cys Asn Ser Leu Asp Gly Ser Asn
 50                  55                  60

Trp Gly Gln Glu Gln Arg Glu Asp His Leu Cys Phe Ser Pro Gly Ser
 65                  70                  75                  80

Glu Val Lys Phe Thr Val Thr Phe Glu Ser Asp Lys Phe Lys Val Lys
                    85                  90                  95

```
Leu Pro Asp Gly His Glu Leu Thr Phe Pro Asn Arg Leu Gly His Ser
            100                 105                 110

His Leu Ser Tyr Leu Ser Val Arg Gly Gly Phe Asn Met Ser Ser Phe
        115                 120                 125

Lys Leu Lys Glu
    130

<210> SEQ ID NO 17
<211> LENGTH: 142
<212> TYPE: PRT
<213> ORGANISM: Homo sapiens

<400> SEQUENCE: 17

Met Ser Leu Leu Pro Val Pro Tyr Thr Glu Ala Ala Ser Leu Ser Thr
1               5                   10                  15

Gly Ser Thr Val Thr Ile Lys Gly Arg Pro Leu Ala Cys Phe Leu Asn
            20                  25                  30

Glu Pro Tyr Leu Gln Val Asp Phe His Thr Glu Met Lys Glu Glu Ser
        35                  40                  45

Asp Ile Val Phe His Phe Gln Val Cys Phe Gly Arg Arg Val Val Met
    50                  55                  60

Asn Ser Arg Glu Tyr Gly Ala Trp Lys Gln Gln Val Glu Ser Lys Asn
65                  70                  75                  80

Met Pro Phe Gln Asp Gly Gln Glu Phe Glu Leu Ser Ile Ser Val Leu
                85                  90                  95

Pro Asp Lys Tyr Gln Val Met Val Asn Gly Gln Ser Ser Tyr Thr Phe
            100                 105                 110

Asp His Arg Ile Lys Pro Glu Ala Val Lys Met Val Gln Val Trp Arg
        115                 120                 125

Asp Ile Ser Leu Thr Lys Phe Asn Val Ser Tyr Leu Lys Arg
    130                 135                 140

<210> SEQ ID NO 18
<211> LENGTH: 139
<212> TYPE: PRT
<213> ORGANISM: Homo sapiens

<400> SEQUENCE: 18

Met Ser Ser Leu Pro Val Pro Tyr Lys Leu Pro Val Ser Leu Ser Val
1               5                   10                  15

Gly Ser Cys Val Ile Ile Lys Gly Thr Pro Ile His Ser Phe Ile Asn
            20                  25                  30

Asp Pro Gln Leu Gln Val Asp Phe Tyr Thr Asp Met Asp Glu Asp Ser
        35                  40                  45

Asp Ile Ala Phe Arg Phe Arg Val His Phe Gly Asn His Val Val Met
    50                  55                  60

Asn Arg Arg Glu Phe Gly Ile Trp Met Leu Glu Glu Thr Thr Asp Tyr
65                  70                  75                  80

Val Pro Phe Glu Asp Gly Lys Gln Phe Glu Leu Cys Ile Tyr Val His
                85                  90                  95

Tyr Asn Glu Tyr Glu Ile Lys Val Asn Gly Ile Arg Ile Tyr Gly Phe
            100                 105                 110

Val His Arg Ile Pro Pro Ser Phe Val Lys Met Val Gln Val Ser Arg
        115                 120                 125

Asp Ile Ser Leu Thr Ser Val Cys Val Cys Asn
    130                 135
```

```
<210> SEQ ID NO 19
<211> LENGTH: 139
<212> TYPE: PRT
<213> ORGANISM: Homo sapiens

<400> SEQUENCE: 19

Met Ser Ser Leu Pro Val Pro Tyr Thr Leu Pro Val Ser Leu Pro Val
1               5                   10                  15

Gly Ser Cys Val Ile Ile Thr Gly Thr Pro Ile Leu Thr Phe Val Lys
                20                  25                  30

Asp Pro Gln Leu Glu Val Asn Phe Tyr Thr Gly Met Asp Glu Asp Ser
            35                  40                  45

Asp Ile Ala Phe Gln Phe Arg Leu His Phe Gly His Pro Ala Ile Met
        50                  55                  60

Asn Ser Cys Val Phe Gly Ile Trp Arg Tyr Glu Glu Lys Cys Tyr Tyr
65                      70                  75                  80

Leu Pro Phe Glu Asp Gly Lys Pro Phe Glu Leu Cys Ile Tyr Val Arg
                85                  90                  95

His Lys Glu Tyr Lys Val Met Val Asn Gly Gln Arg Ile Tyr Asn Phe
            100                 105                 110

Ala His Arg Phe Pro Pro Ala Ser Val Lys Met Leu Gln Val Phe Arg
        115                 120                 125

Asp Ile Ser Leu Thr Arg Val Leu Ile Ser Asp
        130                 135
```

INHIBITORS OF PROTOTYPIC GALECTIN DIMERIZATION AND USES THEREOF

CROSS REFERENCE TO RELATED APPLICATIONS

The present application is a National Entry Application of PCT application No. PCT/CA2016/050587, filed on May 25, 2016, which claims the benefits of U.S. provisional application Ser. No. 62/167,512, filed on May 28, 2015, which are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled 9355-8_ST25.txt, 12,687 bytes in size, generated on Nov. 22, 2017 and filed via EFS-Web, is provided in lieu of a paper copy. This Sequence Listing is hereby incorporated by reference into the specification for its disclosures.

TECHNICAL FIELD

The present invention generally relates to prototypic galectins, and more particularly to the inhibition of galectin-7 dimerization and related applications.

BACKGROUND ART

Cancer is a complex pathology manifested by uncontrolled growth of cells that have undergone various transformations from physiologically normal cells. Several hallmarks provide a methodical and rational approach in studying this disease, namely the sustaining of proliferative signaling, evasion of growth suppressors, resistance to cell death, replicative immortality, angiogenesis, activation of invasion, and metastasis [1]. In recent years, however, strong evidence has highlighted the important role of immune cells present in the tumor micro-environment [2, 3]. For instance, one way that tumor cells can modulate and escape immune destruction is by secretion of various factors such as pro-inflammatory eicosanoids, cytokines, chemokines and other soluble signaling molecules leading to the formation of an immunosuppressive tumor micro-environment [4].

Galectins are multifunctional proteins belonging to the animal lectin family. All galectins share similar binding affinities to β-galactosides and display high amino acid sequence homology among their carbohydrate-binding domains (CRDs) [5]. In mammals, 19 different members have been identified, and 13 of them have been identified in humans. Galectins are divided in three sub-groups according to their structure: prototypic galectins containing one CRD (Gal-1, -2, -5, -7, -10, -13, -14, -15, -16, -17, -19, and -20), tandem-repeat galectins containing two-CRDs covalently linked (Gal-4, -6, -8, -9 and -12) and a chimera-type galectin containing multiple CRDs linked by their amino-terminal domain (Gal-3) [6, 52, 53]. While these proteins perform homeostatic functions inside normal cells, under pathological or stress conditions, cytosolic galectins are released either passively from dead cells or actively via non-classical secretion pathways [7]. Once in the extracellular milieu, they bind all glycosylated growth receptors on the surface of normal and cancer cells to set their signaling threshold [8, 9]. Such properties enable galectins to kill infiltrating immune cells while promoting growth of tumour cells [9]. Galectins are thus ideal targets for effective therapeutics, and new approaches are therefore being developed to modulate their activities [10]. These avenues have focused mainly on carbohydrate-based inhibitors disrupting extracellular galectins, which form multivalent complexes with cell surface glycoconjugates to deliver CRD-dependent intracellular signals that modulate cell activation and survival/apoptosis. Despite decades of research, however, the progression in this field has been very slow. In most cases, these inhibitors are high molecular weight, naturally occurring polysaccharides that are used to specifically block the binding of extracellular galectins to carbohydrate structures [11-14]. Unfortunately, such inhibitors often display low affinity, lack of selectivity for a given galectin due to highly conserved homology among galectin CRDs, and are not effective at targeting CRD-independent functions of galectins. Indeed, several studies have shown that several critical biological processes of galectins are mediated via CRD-independent interactions [15-18].

There is thus a need for novel modulators of galectins, for example inhibitors that targets CRD-independent functions of galectins.

The present description refers to a number of documents, the content of which is herein incorporated by reference in their entirety.

SUMMARY OF THE INVENTION

The present invention provides the following items 1 to 52:

1. A peptide or peptidomimetic of 50 residues of less that inhibits human galectin-7 dimerization, said peptide comprising:
(i) a domain comprising at least 5 residues of the sequence of formula II:

$$Xaa^{14}\text{-}Xaa^{15}\text{-}Xaa^{16}\text{-}Xaa^{17}\text{-}Xaa^{18}\text{-}Xaa^{19}\text{-}Xaa^{20} \quad (II)$$

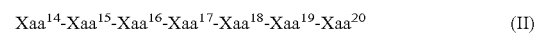

wherein
"-" represents a bond;
$Xaa^{14}$ is L-Leu or D-Leu;
$Xaa^{15}$ is L-Asp or D-Asp;
$Xaa^{16}$ is L-Ser or D-Ser;
$Xaa^{17}$ is L-Val or D-Val;
$Xaa^{18}$ L-Arg or D-Arg;
$Xaa^{15}$ is L-Ile or D-Ile;
$Xaa^{20}$ is L-Phe or D-Phe;
or a domain comprising at least 5 residues of the sequence of formula II in which one of $Xaa^{14}$, $Xaa^{16}$, $Xaa^{17}$, $Xaa^{18}$, $Xaa^{16}$ or $Xaa^{20}$ is mutated;
(ii) a domain comprising at least 5 residues of the sequence of formula I:

$$Xaa^1\text{-}Xaa^2\text{-}Xaa^3\text{-}Xaa^4\text{-}Xaa^5\text{-}Xaa^6\text{-}Xaa^7\text{-}Xaa^8\text{-}Xaa^9\text{-}Xaa^{10}\text{-}Xaa^{11}\text{-}Xaa^{12}\text{-}Xaa^{13} \quad (I)$$

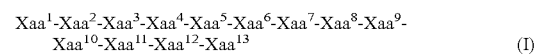

"-" represents a bond;
$Xaa^1$ is L-Ile or D-Ile;
$Xaa^2$ is L-Arg or D-Arg;
$Xaa^3$ is L-Pro or D-Pro;
$Xaa^4$ is Gly;
$Xaa^5$ is L-Thr or D-Thr;
$Xaa^6$ is L-Val or D-Val;
$Xaa^7$ is L-Leu or D-Leu;
$Xaa^8$ is L-Arg or D-Arg;
$Xaa^9$ is L-Ile or D-Ile;
$Xaa^{10}$ is L-Arg or D-Arg;
$Xaa^{11}$ is Gly;
$Xaa^{12}$ is L-Leu or D-Leu;
$Xaa^{13}$ is L-Val or D-Val;

or a domain comprising at least 5 residues of the sequence of formula I in which 1 or 2 residue(s) is/are mutated; or
(iii) a domain comprising at least 5 residues of the sequence of formula III:

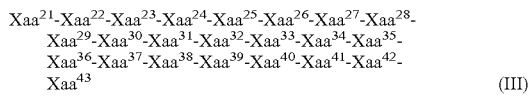

(III)

wherein "-" is a bond;
$Xaa^{21}$ is L-Phe or D-Phe;
$Xaa^{22}$ is L-Glu or D-Glu;
$Xaa^{23}$ is L-Val or D-Val;
$Xaa^{24}$ is L-Leu or D-Leu;
$Xaa^{25}$ is L-Ile or D-Ile;
$Xaa^{26}$ is L-Ile or D-Ile;
$Xaa^{27}$ is L-Ala or D-Ala;
$Xaa^{28}$ is L-Ser or D-Ser;
$Xaa^{29}$ is L-Asp or D-Asp;
$Xaa^{30}$ is L-Asp or D-Asp;
$Xaa^{31}$ is Gly;
$Xaa^{32}$ is L-Phe or D-Phe;
$Xaa^{33}$ is L-Lys or D-Lys;
$Xaa^{34}$ is L-Ala or D-Ala;
$Xaa^{35}$ is L-Val or D-Val;
$Xaa^{36}$ is L-Val or D-Val;
$Xaa^{37}$ is Gly;
$Xaa^{38}$ is L-Asp or D-Asp;
$Xaa^{39}$ is L-Ala or D-Ala;
$Xaa^{40}$ is L-Gln or D-Gln;
$Xaa^{41}$ is L-Tyr or D-Tyr;
$Xaa^{42}$ is L-His or D-His, and
$Xaa^{43}$ is L-His or D-His;
or a domain comprising at least 5 residues of the sequence of formula III in which 1 or 2 residue(s) is/are mutated.
or a salt thereof.

2. The peptide, peptidomimetic or salt thereof of item 1, which comprises a domain comprising at least 5 residues of the sequence of formula II, or a domain of formula II in which one of $Xaa^{14}$, $Xaa^{16}$, $Xaa^{17}$, $Xaa^{18}$, $Xaa^{19}$ or $Xaa^{20}$ is mutated.

3. The peptide, peptidomimetic or salt thereof of item 2, which comprises a domain comprising at least 5 residues of the sequence of formula II, or a domain of formula II in which one of $Xaa^{16}$ or $Xaa^{18}$ is mutated.

4. The peptide, peptidomimetic or salt thereof of item 3, which comprises a domain comprising at least 5 residues of the sequence of formula II.

5. The peptide, peptidomimetic or salt thereof of any one of items 2 to 4, which has 20 residues or less.

6. The peptide, peptidomimetic or salt thereof of item 5, which has 15 residues or less.

7. The peptide, peptidomimetic or salt thereof of item 6, which has 10 residues or less.

8. The peptide, peptidomimetic or salt thereof of item 7, which has 7 residues.

9. The peptide, peptidomimetic or salt thereof of any one of items 1 to 8, which comprises the following domain: Leu-Asp-Ser-Val-Arg-Ile-Phe (SEQ ID NO:1).

10. The peptide, peptidomimetic or salt thereof of item 1, which comprises a domain comprising at least 5 residues of the sequence of formula I, or a domain of formula I in which 1 or 2 residue(s) is/are mutated.

11. The peptide, peptidomimetic or salt thereof of item 10, which comprises a domain comprising at least 5 residues of the sequence of formula I, or a domain of formula I in which 1 residue is mutated.

12. The peptide, peptidomimetic or salt thereof of item 10, which comprises a domain comprising at least 5 residues of the sequence of formula I.

13. The peptide, peptidomimetic or salt thereof of any one of items 10 to 12, which has 20 residues or less.

14. The peptide, peptidomimetic or salt thereof of item 13, which has 15 residues or less.

15. The peptide, peptidomimetic or salt thereof of item 14, which has 13 residues.

16. The peptide, peptidomimetic or salt thereof of any one of items 10 to 15, which comprises the following domain: Ile-Arg-Pro-Gly-Thr-Val-Leu-Arg-Ile-Arg-Gly-Leu-Val (SEQ ID NO:3).

17. The peptide, peptidomimetic or salt thereof of item 1, which comprises a domain comprising at least 5 residues of the sequence of formula IIIA or IIIB:

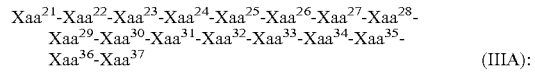

(IIIA):

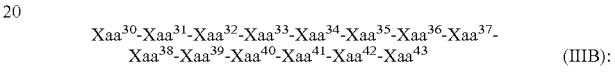

(IIIB):

or a domain comprising at least 5 residues of the sequence of formula IIIA or IIIB in which 1 or 2 residue(s) is/are mutated.
wherein "-" and $Xaa^{21}$ to $Xaa^{43}$ are as defined above.

18. The peptide, peptidomimetic or salt thereof of item 17, which has 20 residues or less.

19. The peptide, peptidomimetic or salt thereof of item 18, which has 15 to 20 residues.

20. The peptide, peptidomimetic or salt thereof of any one of items 10 to 15, which comprises the following domain: Asp-Gly-Phe-Lys-Ala-Val-Val-Gly-Asp-Ala-Gln-Tyr-His-His (SEQ ID NO:5) or Phe-Glu-Val-Leu-Ile-Ile-Ala-Ser-Asp-Asp-Gly-Phe-Lys-Ala-Val-Val-Gly (SEQ ID NO:7).

21. The peptide, peptidomimetic or salt thereof of any one of items 1 to 17, which is of the following formula III:

$Z^1$-D-$Z^2$ wherein
$Z^1$ is H or is an amino-terminal modifying group;
D is the domain of formula I, II or III defined in any one of items 1 to 20; and
$Z^2$ is OH or is a carboxy-terminal modifying group;

22. The peptide, peptidomimetic or salt thereof of item 21, wherein said amino-terminal modifying group is (i) an acyl group (R—CO), wherein R is a hydrophobic moiety, or (ii) an aroyl group (Ar—CO), wherein Ar is an aryl group.

23. The peptide, peptidomimetic or salt thereof of item 21, wherein $Z^1$ is H.

24. The peptide, peptidomimetic or salt thereof of any one of items 21 to 23, wherein said carboxy-terminal modifying group is a hydroxamate group, a nitrile group, an amide group, an alcohol or $CH_2OH$.

25. The peptide, peptidomimetic or salt thereof of item 24, wherein $Z^2$ is $NH_2$.

26. The peptide, peptidomimetic or salt thereof of item 25, which is of one of the following sequences: Leu-Asp-Ser-Val-Arg-Ile-Phe-$NH_2$ (SEQ ID NO:2), Ile-Arg-Pro-Gly-Thr-Val-Leu-Arg-Ile-Arg-Gly-Leu-Val-$NH_2$ (SEQ ID NO:4), Asp-Gly-Phe-Lys-Ala-Val-Val-Gly-Asp-Ala-Gln-Tyr-His-His-$NH_2$ (SEQ ID NO:6) or Phe-Glu-Val-Leu-Ile-Ile-Ala-Ser-Asp-Asp-Gly-Phe-Lys-Ala-Val-Val-Gly-$NH_2$ (SEQ ID NO:8).

27. The peptide, peptidomimetic or salt thereof of item 25, wherein said peptide, peptidomimetic or salt thereof is conjugated to a polyethylene glycol (PEG) chain.

28. A composition comprising the peptide, peptidomimetic or salt thereof of any one of items 1 to 27, and a carrier or excipient.

29. A method for inhibiting the dimerization of native prototypic galectin polypeptides, said method comprising contacting said native prototypic galectin polypeptides with an agent that binds to a domain corresponding to residues 13-25, 86-108 and/or 129-135 of human galectin-7.

30. The method of item 29, wherein said agent is an antibody that specifically binds to an epitope located within a domain corresponding to residues 13-25, 86-108 and/or 129-135 of human galectin-7.

31. The method of item 30, wherein said agent is an antibody that specifically binds to an epitope located within residues 129-135 of human galectin-7.

32. The method of item 29, wherein said agent is the peptide, peptidomimetic or salt thereof of any one of items 1 to 26.

33. A method for inhibiting galectin-7-mediated apoptosis in a cell, said method comprising contacting said cell with the agent defined in any one of items 29 to 32.

34. The method of item 33, wherein said cell is an immune cell.

35. The method of item 34, wherein said immune cell is a T lymphocyte.

36. A method for treating a prototypic galectin-expressing cancer in a subject, said method comprising administering to said subject an effective amount of the agent defined in any one of items 29 to 32.

37. The method of item 36, wherein said prototypic galectin-expressing cancer is a galectin-7-expressing cancer.

38. The method of item 37, wherein said galectin-7-expressing cancer is a breast cancer, an ovarian cancer, or a lymphoma.

39. Use of the agent defined in any one of items 29 to 32 for inhibiting the dimerization of native galectin-7 polypeptides.

40. Use of the agent defined in any one of items 29 to 32 for the manufacture of a medicament for inhibiting the dimerization of native galectin-7 polypeptides.

41. Use of the agent defined in any one of items 29 to 32 for inhibiting galectin-7-mediated apoptosis in a cell.

42. Use of the agent defined in any one of items 29 to 32 for the manufacture of a medicament for inhibiting galectin-7-mediated apoptosis in a cell.

43. The use of item 41 or 42, wherein said cell is an immune cell.

44. The use of item 43, wherein said immune cell is a T lymphocyte.

45. Use of the agent defined in any one of items 29 to 32 for treating a prototypic galectin-expressing cancer in a subject.

46. Use of the agent defined in any one of items 29 to 32 for the manufacture of a medicament for treating a prototypic galectin-expressing cancer in a subject.

47. The use of item 45 or 46, wherein said prototypic galectin-expressing cancer is a galectin-7-expressing cancer.

48. The use of item 47, wherein said galectin-7-expressing cancer is a breast cancer, an ovarian cancer, or a lymphoma.

49. A method for determining whether a test agent that may be used to inhibit a biological, physiological and/or pathological process that involves prototypic galectin dimerization, said method comprising:
    contacting a prototypic galectin polypeptide with said test agent; and
    determining whether said test agent binds to prototypic galectin polypeptide through a domain corresponding to residues 13-25, 86-108 and/or 129-135 of galectin-7,
    wherein the binding of said test agent to said prototypic galectin polypeptide is indicative that said test agent that may be used to inhibit a biological, physiological and/or pathological process that involves prototypic galectin dimerization.

50. The method of item 49, wherein said prototypic galectin is galectin-7.

51. The method of item 49 or 50, wherein said method comprises determining whether said test agent binds to said prototypic galectin polypeptide through a domain corresponding to residues 129-135 of galectin-7.

52. The method of any one of items 49 to 51, wherein said method is for determining whether the test agent may be used to inhibit galectin-7-mediated apoptosis in a cell and/or treat a galectin-7-expressing cancer in a subject.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A Dimer formation of recombinant hGal-7 and hGal-1 at increasing concentrations were compared by polyacrylamide gel electrophoresis in low-sodium dodecyl sulfate (SDS) conditions. FIG. 1B: Structural representation of the hGal-7 (PDB 1BKZ) and hGal-1 (PDB 3W58) dimers with residues 129-135 highlighted (balls and sticks) on the hGal-7 dimer interface. Dimer formation in hGal-7 proceeds through a "back-to-back" topology of the monomers while hGal-1 adopts a "side-by-side" structural arrangement, affording additional specificity for galectin inhibition. FIG. 1C: Molecular interactions implicated in the wild-type hGal-7 dimer interface between residues 129-135 of the first hGal-7 monomer and facing residues on the second hGal-7 monomer (PDB 1BKZ). Hydrogen bonding and electrostatic interactions are identified as dashed lines. The side chain of Phe135 is also involved in a number of van der Waals interactions. The structures were prepared using PyMOL.

FIGS. 2A to 2D show the dose-dependent disruption of the hGal-7 dimer in the presence of hGal-$7_{(13-25)}$, hGal $7_{(85-102)}$, hGal-$7_{(95-108)}$ or hGal-$7_{(129-135)}$ peptides. FIGS. 2A and 2B: The recombinant hGal-7 (0.5 µM) was incubated with increasing concentrations of hGal-$7_{(129-135)}$ (FIG. 2A), hGal-$7_{(13-25)}$, hGal-$7_{(85-102)}$ or hGal-$7_{(95-108)}$ (FIG. 2B) in 20 mM potassium phosphate buffer (pH 7.1). FIG. 2C: Incubation of the recombinant hGal-1 and hGal-$7_{(129-135)}$ was performed in the same potassium phosphate buffer. The effect of hGal-$7_{(129-135)}$ on the monomeric and dimeric forms of hGal-7/hGal-1 was assessed by Western blotting in in low-SDS conditions with respective antibodies. The hGal-1 film was overexposed. PACAP$_{28-38}$ was the control peptide used in order to ensure the specificity of hGal-$7_{(129-135)}$. FIG. 2D: Recombinant hGal-7 (0.5 µM) was also incubated with increasing concentrations of hGal-$7_{(129-135)}$ in 0.1 mM lactose solution.

FIG. 2E: The recombinant hGal-7 (0.5 µM) and Bcl-2 were incubated with increasing concentrations of hGal-$7_{(129-135)}$ in 20 mM potassium phosphate buffer (pH 7.1). The effect of hGal-$7_{(129-135)}$ on the homodimerization and heterodimerization (with Bcl-2) of hGal-7 was assessed by Western blotting in low-SDS conditions with an anti-Gal-7 antibody. Results depicted in FIGS. 2A to 2D are representative of three independent experiments.

FIG. 4A: Histogram showing the mean fluorescence intensities (MFI) of cells due to fluorescein isothiocyanate (FITC)-labeled hGal-7 binding. FIG. 4B: Flow cytometry histogram displaying the fluorescence (FL1) of the cell population due to FITC-labeled hGal-7 binding. Recombinant hGal-7 conjugated to FITC (0.1 μM) was pre-incubated with hGal-7$_{(129-135)}$. Jurkat T cells were then harvested in PBS (sodium-azide 0.01%) and incubated for 30 min with their respective dilutions before flow cytometry analysis. Results are representative of three independent experiments. Error bars represent standard deviation.

FIG. 5A: Recombinant hGal-7 was pre-incubated with the respective peptide concentrations prior to its addition to Jurkat T cells for 4 h at 37° C. in RPMI serum-free media. Apoptosis was monitored by measuring Parp-1 cleavage through Western blotting. FIG. 5B: The peptide PACAP$_{28-38}$ was used as a control to ensure the specificity of hGal-7$_{(129-135)}$. Flow cytometry histogram showing Annexin V (AV) (FL1) and propidium iodide (PI) (FL3) labeling of Jurkat T cells in the presence of hGal-7 with or without hGal-7$_{(129-135)}$ treatments. Cells in the lower right quadrant are representative of AV-positive, early apoptotic cells. Cells in the upper right quadrant indicate AV-positive/PI-positive, late apoptotic cells. FIG. 5C: Histogram showing the average percentage of AV positive Jurkat T cells was obtained by adding the percentage of cells found in the lower and the upper right quadrants. Results are representative of three independent experiments. Error bars represent standard deviation.

FIG. 6C: to ensure denaturing conditions, hGal-7 was also migrated in a 0.1% SDS gel and 0.1% SDS running buffer for 1 h at 150 V, while the protein was treated with β-mercaptoethanol and heated for 10 min at 95° C., prior to loading the gel.

FIG. 7A: Recombinant hGal-7 (0.5 μM) was incubated with increasing concentrations of hGal-7$_{(129-135)}$ in 20 mM potassium phosphate buffer (pH 7.1). Western blotting in low-SDS conditions assessed dimer disruption of hGal-7. FIG. 7B: Recombinant hGal-1 (0.5 μM) was incubated with increasing concentrations of hGal-7$_{(129-135)}$ in 20 mM potassium phosphate buffer (pH 7.1). Western blotting in low-SDS conditions assessed dimer disruption of hGal-1. Results are representative of two independent experiments.

FIG. 8A: Flow cytometry histogram showing propidium iodide (PI) (FL3) labeling of Jurkat T cells without or with 200 μM of hGal-7$_{(129-135)}$. FIG. 8B: Histogram showing the average percentage of Annexin-V (AV) positive Jurkat T cells in the presence of increasing concentrations of hGal-7$_{(129-135)}$. FIG. 8C: Flow cytometry histogram showing PI (FL3) labeling of Jurkat T cells without or with 200 μM of PACAP$_{28-38}$. FIG. 8D: Histogram showing the average percentage of AV-positive Jurkat T cells in the presence of increasing concentrations of PACAP$_{28-38}$. The percentage of cell death was obtained as described above. Error bars represent standard deviation. Significance was calculated with respect to AF samples. Results are representative of three independent experiments.

FIG. 10A shows the amino acid sequence of human galectin-7 (NCBI Reference Sequence: NP_ 002298.1, SEQ ID NO:14), with the domains corresponding to residues 13-25, 85-108 and 129-135 being underlined.

FIG. 10B shows the nucleotide sequence of the cDNA encoding human galectin-7 (NCBI Reference Sequence: NM_ 002307.3, SEQ ID NO:13), with the coding sequence in bold.

FIG. 11 shows an amino acid sequence alignment of the human prototypic galectins (galectin-1, 2, 7, 10, 13 and 14). The regions corresponding to residues 13-25, 85-108 and 129-135 of human galectin-7 are indicated by the brackets. Galectin-1=SEQ ID NO:15; Galectin-2=SEQ ID NO:16; Galectin-10=SEQ ID NO:17; Galectin-13=SEQ ID NO:18; Galectin-14=SEQ ID NO:19).

FIGS. 12A and 12B: detection of hGal-7/Bcl-2 heterodimers in the presence of the indicated amounts of recombinant Bcl-2 using an anti-gal-7 antibody (FIG. 12A) or an anti-Bcl-2 antibody (FIG. 12B). FIG. 12C: the recombinant hGal-7 and Bcl-2 (each at 0.5 μM) were incubated with increasing concentrations of hGal-7$_{(129-135)}$ in 20 mM potassium phosphate buffer (pH 7.1). The effect of hGal-7$_{(129-135)}$ on the homodimerization and heterodimerization (with Bcl-2) of hGal-7 was assessed by Western blotting in low-SDS conditions with an anti-Gal-7 antibody.

DISCLOSURE OF INVENTION

Figure 1A:
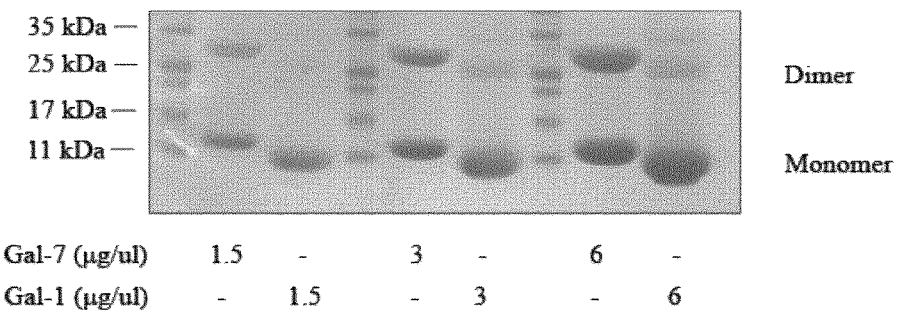
FIGS. 1A to C show the dimeric structure of hGal-7.

The use of the terms "a" and "an" and "the" and similar referents in the context of describing the invention are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language ("e.g.", "such as", etc.) provided herein, is intended merely to better illustrate the invention and does not pose a limitation on the scope of the invention unless otherwise claimed.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

Unless otherwise defined, all technical and scientific terms used herein have the same meaning as commonly understood by one of ordinary skill in the art to which this invention belongs.

Any and all combinations and subcombinations of the embodiments and features disclosed herein are encompassed by the present invention.

In the studies described herein, the present inventors have shown that peptides that target specific domains of galectin-7, more specifically the dimer interface region corresponding to residues 13-25, 86-102, 95-108 and 129-135 of human galectin-7, disrupt the formation of galectin-7 dimers and its pro-apoptotic function.

Accordingly, in a first aspect, the present invention provides an agent that binds to a domain corresponding to residues 13-25, 86-102, 95-108 or 129-135 of human galectin-7 and inhibits the dimerization of a prototypic galectin.

The term "prototypic" or "prototypical" galectins refer to galectins that form homodimers, consisting of two identical galectin subunits that have associated with one another. The mammalian galectins that fall under this category are galectin-1, -2, -5, -7, -10, -11, -13, -14, -15, -16, -17, -19, and -20 (galectin-5, -11, -15, -16, -19, and -20 are not found in humans).

Human galectin-7 (hGal-7) is a 15 kDa prototype galectin with a single CRD, monomeric but capable of dimerization in solution. It was first reported in an effort to identify markers of keratinocyte differentiation. Galectin-7 involvement in the maintenance of the pluristratified epithelia and epidermal stratification has highlighted its role in wound healing. It was proven to be an efficient growth factor with therapeutic implications. Some of the more recent advances on galectin-7 have shown its implication in apoptosis induction in various types of cell. Galectin-7 expression is induced upon UV radiation and regulated by p53, therefore showing high levels in certain types of cancer. hGal-7 has attracted more interest in cancer because its preferential expression in epithelial tissues and carcinoma, it is found in the nucleus of many cancer cells, including hypopharyngeal (HSCCs) and laryngeal (LSCCs) squamous cell carcinomas tissues, colon carcinoma cells (DLD-1), cervical adenocarcinoma (HeLa), epithelial ovarian cancer tissues and oral epithelial dysplasia tissues (Saussez S et al. *Histopathology* 52: 483-493, 2008; Kuwabara I et al. *J Biol Chem* 277: 3487-3497, 2002; Kim H J et al. *Anticancer Res* 33: 1555-1561, 2013; de Vasconcelos Carvalho M et al. *J Oral Pathol Med* 42: 174-179, 2013). Galectin-7 is also observed in the cytosol of colon carcinoma cell line (DLD-1), cervical adenocarcinoma cells (HeLa), epithelial ovarian cancer and oral epithelial dysplasia tissues. (hlen M et al. *Nat Biotechnol* 28: 1248-1250, 2010; Kuwabara I et al. *J Biol Chem* 277: 3487-3497, 2002; Kim H J et al. *Anticancer Res* 33: 1555-1561, 2013; de Vasconcelos Carvalho M, et al. *J Oral Pathol Med* 42: 174-179, 2013.). It is also detected in mitochondrial fractions, most notably in the case of human colorectal carcinoma and cervical adenocarcinoma cell lines (HCT116, HeLa) and the HaCaT keratinocyte cell line (Villeneuve C et al. *Mol Biol Cell* 22: 999-1013, 2011). Galectin-7 has been shown to be involved in cancer development, for example in the growth stimulation of lymphomas (Moisan S, et al., *Leukemia.* 2003; 17:751-759; Demers M, et al., *Cancer Res.* 2005; 65:5205-5210) and the invasive behavior of ovarian cancer cells (Labrie, M., et al., Oncotarget, 2014. 5(17): p. 7705-21) Galectin-7 was also described as a key element in aggressive metastasis following its overexpression in breast carcinomas (Demers M, et al., *Am J Pathol.* 2010; 176:3023-3031), and thus represents a potential therapeutic target. In an embodiment, the agents disclosed herein may be used for the treatment of any of the diseases/cancers defined above.

The expression "domain corresponding to residues 13-25, 86-102, 95-108 or 129-135 of human galectin-7" refers to the domain present any of the prototypic galectins and that corresponds, e.g., based on sequence alignment, to residues 13-25, 86-102, 95-108 or 129-135 of galectin-7. In an embodiment, corresponding domains may be identified for example by aligning the sequences of the different prototypic galectins (see FIG. 11). The domains corresponding to residues 13-25, 86-108 (i.e. 86-102 and 95-108) or 129-135 of human galectin-7 are indicated by the brackets. For example, the domain corresponding to residues 129-135 of human galectin-7 in galectin-1 comprises the sequence: Ile-Lys-Cys-Val-Ala-Phe-Asp(128-134).

The expression "inhibits the dimerization of a prototypic galectin" refers to the inhibition of the homodimerization of the prototypic galectin (e.g., galectin-7), and/or to the heterodimerization of the prototypic galectin (e.g., galectin-7) with other proteins, such as members of the bcl-2 family (reference [15]). In an embodiment, the homodimerization of the prototypic galectin is inhibited. In another embodiment, the heterodimerization of the prototypic galectin is inhibited. In another embodiment, both the homodimerization and heterodimerization of the prototypic galectin are inhibited.

The agent includes any compound that binds to a domain corresponding to residues 13-25, 86-102, 95-108, and/or 129-135 of human galectin-7 and inhibits prototypic galectin (e.g., galectin-7) dimerization. Without being so limited, such inhibitors include proteins (e.g., dominant negative, inactive variants), peptides, small molecules, antibodies, antibody fragments, etc.

In an embodiment, the agent that inhibits prototypic galectin (e.g., galectin-7) dimerization is a neutralizing antibody directed against (or specifically binding to) to a domain corresponding to residues 13-25, 86-102, 95-108 and/or 129-135 of human galectin-7. The term "antibody" or "immunoglobulin" is used in the broadest sense, and covers monoclonal antibodies (including full-length monoclonal antibodies), polyclonal antibodies, humanized antibodies, CDR-grafted antibodies, chimeric antibodies, multispecific antibodies, and antibody fragments so long as they exhibit the desired biological activity (e.g., blocking prototypic galectin (e.g., galectin-7) dimerization, neutralizing an activity related to prototypic galectin (e.g., galectin-7) dimerization). Antibody fragments comprise a portion of a full-length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies. In an embodiment, the antibody is a monoclonal antibody. In another embodiment, the antibody is a humanized or CDR-grafted antibody.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories).

Polyclonal antibodies are preferably raised in animals by multiple subcutaneous (s.c.), intravenous (i.v.) or intraperitoneal (i.p.) injections of the relevant antigen (e.g., a polypeptide comprising a sequence corresponding to residues 13-25, 86-102, 95-108, and/or 129-135 of human galectin-7, or an immunogenic fragment thereof, such as a fragment of at least 5, 6, 7, 8, 9 or 10 residues) with or without an adjuvant. It may be useful to conjugate the relevant antigen to a protein that is immunogenic in the species to be immunized (sometimes referred to as a carrier), e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen (a peptide/polypeptide comprising a sequence corresponding to residues 13-25, 86-102, 95-108, and/or 129-135 of human galectin-7, or an immunogenic fragment thereof, such as a fragment of at least 5, 6, 7, 8, 9 or 10 residues), immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with 1/5 to 1/10 of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

A human chimeric antibody can be produced in the following manner. cDNA encoding heavy chain variable region ($V_H$) and light chain variable region ($V_L$) obtained from a hybridoma derived from non-human animal cells producing monoclonal antibodies, the cDNA is inserted to each of expression vectors for animal cells having DNA encoding a heavy chain constant region ($C_H$) and light chain constant region ($C_L$) of a human antibody so as to construct a human chimeric antibody expression vector, and this vector is introduced to animal cells to express the human chimeric antibody.

A humanized antibody refers to an antibody that is obtained by grafting the amino acid sequence of the complementary determining region (CDR) of $V_H$ and $V_L$ of a non-human animal antibody to CDR corresponding to $V_H$ and $V_L$ of a human antibody. The region other than CDR of $V_H$ and $V_L$ is called a framework region (hereinbelow, described as "FR"). A humanized antibody can be produced in the following manner. cDNA encoding an amino acid sequence of $V_H$ which consists of an amino acid sequence of CDR of $V_H$ of a non-human antibody and an amino acid sequence of FR of $V_H$ of any human antibody, and cDNA encoding an amino acid sequence of $V_L$ which consists of an amino acid sequence of CDR of $V_L$ of a non-human animal antibody and an amino acid sequence of FR of $V_L$ of any human antibody are constructed, these cDNAs are inserted respectively into expression vectors for animal cells having DNA encoding $C_H$ and $C_L$ of a human antibody so as to construct a humanized antibody expression vector, and this vector is inserted into animal cells to express the humanized antibody.

Based on the sequences of the human prototypic galectin polypeptides (see FIG. 11), and more particularly of amino acids corresponding to residues 13-25, 86-102, 95-108, and 129-135 of human galectin-7, the skilled person would be able to generate antibodies directed against this polypeptide/domain(s), which in turn may be used to block its dimerization and neutralize its activity.

In an embodiment, the agent that inhibits prototypic galectin (e.g., galectin-7) dimerization is an inactive prototypic galectin peptide or polypeptide (e.g., dominant negative), or a nucleic acid (e.g., mRNA) encoding such an inactive prototypic galectin peptide or polypeptide, which may compete with the native prototypic galectin (e.g., galectin-7) for dimerization (by binding to the domain(s) corresponding to amino acids 13-25, 86-102, 95-108 and/or 129-135 of galectin-7), but fails to induce the signaling cascade and biological activity of the native prototypic galectin (e.g., galectin-7) homodimers. Administration of the inactive prototypic galectin (e.g., galectin-7) peptide or polypeptide may be direct (administration of the polypeptide itself) or indirect, for example via administration of a nucleic acid encoding the inactive prototypic galectin (e.g., galectin-7) peptide or polypeptide.

In another embodiment, the agent that inhibits prototypic galectin (e.g., galectin-7) dimerization is a peptide or peptidomimetic (or a salt thereof) of 50 residues of less that inhibits human prototypic galectin (e.g., galectin-7) dimerization, the peptide comprising: (i) a domain comprising at least 5 residues of the sequence of formula I

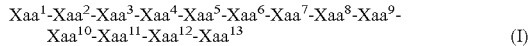  (I)

wherein "-" is a bond; $Xaa^1$ is L-Ile, D-Ile or an analog thereof; $Xaa^2$ is L-Arg, D-Arg or an analog thereof; $Xaa^3$ is L-Pro, D-Pro or an analog thereof; $Xaa^4$ is Gly or an analog thereof; $Xaa^5$ is L-Thr, D-Thr or an analog thereof; $Xaa^6$ is L-Val, D-Val or an analog thereof; $Xaa^7$ is L-Leu, D-Leu or an analog thereof; $Xaa^8$ is L-Arg, D-Arg or an analog thereof; $Xaa^9$ is L-Ile, D-Ile or an analog thereof; $Xaa^{10}$ is L-Arg, D-Arg or an analog thereof; $Xaa^{11}$ is Gly or an analog thereof; $Xaa^{12}$ is L-Leu, D-Leu or an analog thereof; $Xaa^{13}$ is L-Val, D-Val or an analog thereof; or a domain of formula I in which 1 or 2 residue(s) is/are mutated;

(ii) a domain comprising at least 5 residues of the sequence of formula II:

$$Xaa^{14}\text{-}Xaa^{15}\text{-}Xaa^{16}\text{-}Xaa^{17}\text{-}Xaa^{18}\text{-}Xaa^{19}\text{-}Xaa^{20}$$  (II)

wherein "-" is a bond; $Xaa^{14}$ is L-Leu, D-Leu or an analog thereof; $Xaa^{15}$ is L-Asp, D-Asp or an analog thereof; $Xaa^{16}$ is L-Ser, D-Ser or an analog thereof; $Xaa^{17}$ is L-Val, D-Val or an analog thereof; $Xaa^{18}$ L-Arg, D-Arg or an analog thereof; $Xaa^{19}$ is L-Ile, D-Ile or an analog thereof; and $Xaa^{20}$ is L-Phe, D-Phe or an analog thereof; or a domain of formula II in which one of $Xaa^{14}$, $Xaa^{16}$, $Xaa^{17}$, $Xaa^{18}$, $Xaa^{19}$ or $Xaa^{20}$ is mutated;

(iii) a domain comprising at least 5 residues of the sequence of formula III:

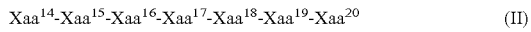  (III)

wherein "-" is a bond; $Xaa^{21}$ is L-Phe, D-Phe or an analog thereof; $Xaa^{22}$ is L-Glu, D-Glu or an analog thereof; $Xaa^{23}$ is L-Val, D-Val or an analog thereof; $Xaa^{24}$ is L-Leu, D-Leu or an analog thereof; $Xaa^{25}$ is L-Ile, D-Ile or an analog thereof; $Xaa^{26}$ is L-Ile, D-Ile or an analog thereof; $Xaa^{27}$ is L-Ala, D-Ala or an analog thereof; $Xaa^{28}$ is L-Ser, D-Ser or an analog thereof; $Xaa^{29}$ is L-Asp, D-Asp or an analog thereof; $Xaa^{30}$ is L-Asp, D-Asp or an analog thereof; $Xaa^{31}$ is Gly or an analog thereof; $Xaa^{32}$ is L-Phe, D-Phe or an analog thereof; $Xaa^{33}$ is L-Lys, D-Lys or an analog thereof; $Xaa^{34}$ is L-Ala, D-Ala or an analog thereof; $Xaa^{35}$ is L-Val, D-Val or an analog thereof; $Xaa^{36}$ is L-Val, D-Val or an analog thereof; $Xaa^{37}$ is Gly or an analog thereof; $Xaa^{38}$ is L-Asp, D-Asp or an analog thereof; $Xaa^{39}$ is L-Ala, D-Ala or an analog thereof; $Xaa^{40}$ is L-Gln, D-Gln or an analog thereof; $Xaa^{41}$ is L-Tyr, D-Tyr or an analog thereof; $Xaa^{42}$ is L-His, D-His or an analog thereof, and $Xaa^{43}$ is L-His, D-His or an analog thereof, or a domain of formula III in which in which 1 or 2 residue(s) is/are mutated.

In an embodiment, the peptide comprises a domain comprising at least 5 residues of the sequence of formula IIIA or IIIB:

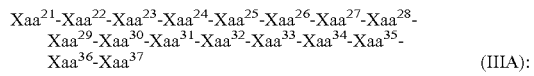  (IIIA):

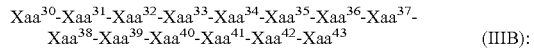  (IIIB):

wherein "-" and $Xaa^{21}$ to $Xaa^{43}$ are as defined above.

As used herein, the term "peptidomimetic" refers to a compound comprising a plurality of amino acid residues (naturally- and/or non-naturally-occurring amino acids, amino acid analogs) joined by a plurality of peptide and/or non-peptide bonds. Peptidomimetics typically retain the polarity, three-dimensional size and functionality (bioactivity) of their peptide equivalents, but one or more of the peptide bonds/linkages have been replaced, often by more stable linkages. Generally, the bond which replaces the amide bond (amide bond surrogate) conserves many or all of the properties of the amide bond, e.g. conformation, steric bulk, electrostatic character, potential for hydrogen bonding, etc. Typical peptide bond replacements include esters, polyamines and derivatives thereof as well as substituted alkanes and alkenes, such as aminomethyl and ketomethylene. For example, the above-mentioned domain or peptide may have one or more peptide linkages replaced by linkages such as —$CH_2NH$—, —$CH_2S$—, —$CH_2$—$CH_2$—, —$CH$=$CH$— (cis or trans), —$CH_2SO$—, —$CH(OH)$$CH_2$—, or —$COCH_2$—. Such peptidomimetics may have greater chemical stability, enhanced biological/pharmacological properties (e.g., half-life, absorption, potency, efficiency, etc.) and/or reduced antigenicity relative its peptide equivalent.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally-occurring amino acids are glycine, alanine, valine, leucine, isoleucine, serine, threonine, etc. Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylic acid, beta-2-thienylalanine, methionine sulfoxide, L-homoarginine (Hoarg), N-acetyl lysine, 2-amino butyric acid, 2-amino butyric acid, 2,4-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3- diaminobutyric acid (D- or L-), etc. These amino acids are well known in the art of biochemistry/peptide chemistry.

The term "analog" when used in reference to an amino acid refers to synthetic amino acids providing similar side chain functionality (i.e., structurally similar) as the "native" amino acid and which can be substituted for an amino acid in the formation of a peptidomimetic. Amino acid analogs include, without limitation, β-amino acids and amino acids, in which the amino or carboxy group is substituted by a similarly reactive group or other groups (e.g., substitution of the primary amine with a secondary or tertiary amine, or substitution of the carboxy group with an ester).

For example, aromatic amino acids may be replaced with D- or L-naphthylalanine, D- or L-homophenylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is substituted or unsubstituted methyl, ethyl, propyl, hexyl, butyl, pentyl, isopropyl, iso-butyl, or iso-pentyl.

Non-carboxylate amino acids can be made to possess a negative charge, as provided by phosphono- or sulfated (e.g., $-SO_3H$) amino acids, which are to be considered as non-limiting examples.

Other substitutions may include unnatural alkylated amino acids, made by combining an alkyl group with a natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine. In addition, any amide linkage in the peptide may be replaced by a ketomethylene, hydroxyethyl, ethyl/reduced amide, thioamide or reversed amide moieties, (e.g., (—C═O)—CH$_2$—), (—CHOH)—CH$_2$—), (CH$_2$—CH$_2$—), (—C═S)—NH—), or (—NH—(—C═O) for (—C═O)—NH—)).

Covalent modifications of the above-mentioned peptide or peptidomimetic (or a salt thereof) are thus included within the scope of the present invention. Such modifications may be introduced into the above-mentioned peptide, peptidomimetic or salt thereof for example by reacting targeted amino acid residues of the peptide with an organic derivatizing agent that is capable of reacting with selected side chains or terminal residues. The following examples of chemical derivatives are provided by way of illustration and not by way of limitation.

Cysteinyl residues may be reacted with alpha-haloacetates (and corresponding amines), such as 2-chloroacetic acid or chloroacetamide, to give carboxymethyl or carboxyamidomethyl derivatives. Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0. Lysinyl and amino terminal residues may be reacted with compounds such as succinic or other carboxylic acid anhydrides. Other suitable reagents for derivatizing alpha-amino-containing residues include compounds such as imidoesters, e.g., methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues is typically performed in alkaline conditions because of the high pKa of the guanidine functional group. Furthermore, these reagents may react with the groups of lysine as well as the arginine epsilon-amino group. The specific modification of tyrosinyl residues per se is well-known, such as for introducing spectral labels into tyrosinyl residues by reaction with aromatic diazonium compounds or tetranitromethane. N-acetylimidazol and tetranitromethane may be used to form O-acetyl tyrosinyl species and 3-nitro derivatives, respectively. Tryptophan residues may be methylated at position 2 (sometimes referred to as 2Me-Trp or Mrp).

Carboxyl side groups (aspartyl or glutamyl) may be selectively modified by reaction with carbodiimides (R'—N═C═N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions. Glutaminyl and asparaginyl residues may be frequently deamidated to the corresponding glutamyl and aspartyl residues. Other modifications of the above-mentioned peptide analog/azasulfurylpeptide may include hydroxylation of proline and lysine, phosphorylation of hydroxyl groups of seryl or threonyl residues, methylation of the alpha-amino groups of lysine, arginine, and histidine side chains acetylation of the N-terminal amine, methylation of main chain amide residues (or substitution with N-methyl amino acids) and, in some instances, amidation of the C-terminal carboxyl groups, according to known method steps.

Analogs of histidine include those described in Ikeda et al., Protein Eng. (2003) 16 (9): 699-706 (e.g., β-(1,2,3-triazol-4-yl)-DL-alanine), those described in Stefanucci et al., *Int. J. Mol. Sci.* 2011, 12(5), 2853-2890 (aza-histidine, homo-histidine, β$^2$-homo-histidine, β$^3$-homo-histidine, Nor-histidine), N-imidazolyl alanine, methyl histidine, dimethyl histidine, C-triazolyl alanine, histidine methyl ester, histidinol, and histidinamide.

Analogs of tryptophan includes 2-Me-Trp (or Mrp), 5-Methyl-DL-tryptophan, azatryptophan (7-azatryptophan), hydroxytryptophan (5-hydroxytryptophan), fluorotryptophan, aminotryptophan, tryptamine and desaminotryptophan, α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl tryptophan; D-1,2,3,4-tetrahydro-norharman-3-carboxylic acid; 6-methoxy-1,2,3,4-tetrahydronorharman-1-carboxylic acid; L-1,2,3,4-tetrahydro-norharman-3-carboxylic acid; 5-methoxy-2-methyl-tryptophan; and 6-chloro-L-tryptophan.

Analogs of alanine include β-alanine, aminoisobutyric acid (α or β), methylalanine and t-butylalanine.

Analogs of phenylalanine include β-methyl-phenylalanine, β-hydroxyphenylalanine, α-methyl-3-methoxy-DLphenylalanine, α-methyl-D-phenylalanine, α-methyl-L-phenylalanine, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2,4,5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-cyano-D-phenylalanine, 3-cyano-L-phenylalanine, 3-fluoro-D-phenylalanine, 3-fluoro-L-phenylalanine, 3-iodo-D-phenylalanine, 3-iodo-L-phenylalanine, 3-methyl-D-phenylalanine, 3-methyl-L-phenylalanine, 3-nitro-D-phenylalanine, 3-nitro-L-phenylalanine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, 3,3-diphenylalanine.

Analogs of lysine include the related amino acid arginine and analogs thereof such as citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxocyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH(asymmetrical); Arg(Me)$_2$-OH (symmetrical); Lys(ivDde)-OH; Lys(Me)$_2$-OH.HCl; Lys(Me$_3$)-OH chloride; Nω-nitro-D-arginine; and Nω-nitro-L-arginine.

In embodiments, the domain, peptide or peptidomimetic of the present invention include domains, peptides or peptidomimetics with altered sequences containing substitutions of functionally equivalent amino acid residues, relative to the above-mentioned domains, peptides or peptidomimetics. For example, one or more amino acid residues within the sequence can be substituted by another amino acid of a similar polarity (having similar physico-chemical properties) which acts as a functional equivalent, resulting in a silent alteration. Substitution for an amino acid within the sequence may be selected from other members of the class to which the amino acid belongs. For example, positively charged (basic) amino acids include arginine, lysine and histidine (as well as homoarginine and ornithine). Nonpolar (hydrophobic) amino acids include leucine, isoleucine, alanine, phenylalanine, valine, proline, tryptophan and methionine. Uncharged polar amino acids include serine, threonine, cysteine, tyrosine, asparagine and glutamine. Negatively charged (acidic) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

The above-mentioned domain, peptide or peptidomimetic (or salt thereof) may comprise only L-amino acids, only D-amino acids, or a mixture of L- and D-amino acids. In an embodiment, the above-mentioned domain, peptide or peptidomimetic (or salt thereof) comprises at least one D-amino acid (e.g., 1, 2, 3, 4, 5 or more D-amino acids). The presence of one or more D-amino acids typically results in peptides having increased stability (e.g., in vivo) due to decreased susceptibility to protease/peptidase cleavage, but which retain biological activity. In another embodiment, the domain, peptide or peptidomimetic (or salt thereof) comprise only L-amino acids.

In embodiments, the above-mentioned peptide or peptidomimetic is in the form of a salt, e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the analog, or may be prepared separately by reacting a free base function with a suitable acid. Many of the peptides or peptidomimetics disclosed herein are capable of forming acid and/or base salts by virtue of the presence of amino and/or carboxyl groups or groups similar thereto.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, decanoate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, octanoate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

In an embodiment, the above-mentioned peptide or peptidomimetic (or salt thereof) comprises one domain of formula I, II, or III as defined above. In an embodiment, the above-mentioned peptide or peptidomimetic (or salt thereof) comprises two or more (e.g., 2, 3, 4 or 5) domains (repeats) of formula I, II, or III as defined above.

In embodiments, the above-mentioned peptide or peptidomimetic (or salt thereof) may comprise, further to the domain of formula I or II defined above, one more amino acids (naturally occurring or synthetic) covalently linked to the amino- and/or carboxy-termini of said domain. In an embodiment, the above-mentioned peptide or peptidomimetic (or salt thereof) comprises up to 43 additional amino acids at the N- and/or C-termini to the domain of formula (I), (II), or (I) defined above. In further embodiments, the above-mentioned peptide or peptidomimetic (or salt thereof) comprises up to 40, 35, 30, 25, 20, 19, 18, 17, 16, 15, 14, 13, 12, 11, 10, 9, 8, 7, 6, 5, 4, 3, 2, or 1 additional amino acids at the N- and/or C-termini of the domain of formula (I), (II), or (III) defined above. In an embodiment, the above-mentioned peptide or peptidomimetic (or salt thereof) contains about 45 residues or less, in further embodiments about 40, 35, 30, 25, 20, 19, 18, 17, 16 or 15 residues or less. In an embodiment, the above-mentioned peptide or peptidomimetic (or salt thereof) contains between about 7 residues to about 15 residues, for example about 7, 8, 9, 10, 11, 12, 13, 14 or 15 residues. In an embodiment, the peptide or peptidomimetic (or salt thereof) comprises, or consists of, 5, 6, 7, 8, 9 or 10 to 20, 25, 30, 35, 40, 45, or 50 residues.

In embodiments, the N- and/or C-terminal amino acids of the above-mentioned peptide or peptidomimetic (or salt thereof) may be modified, for example by amidation, acetylation, acylation or any other modifications known in the art.

Accordingly, in another aspect, the present invention provides a peptide or peptidomimetic (or salt thereof) of formula (IV):

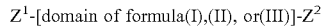

wherein $Z^1$ is H (i.e. the peptide or peptidomimetic has a native $NH_2$ terminal) an amino-terminal modification; and $Z^2$ is OH (i.e. the peptide or peptidomimetic has a native COOH terminal) or a carboxy-terminal modification.

In an embodiment, the amino terminal residue (i.e., the free amino group at the N-terminal end) of the peptide or peptidomimetic (or salt thereof) is modified (e.g., for protection against degradation), for example by covalent attachment of a moiety/chemical group ($Z^1$). In an embodiment, the amino-terminal modification ($Z^1$) is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), in a further embodiment an acetyl group ($CH_3$—CO—, Ac). In another embodiment, the peptide or peptidomimetic (or salt thereof) has a native $NH_2$ terminal, i.e. $Z^1$ is H.

In an embodiment, the carboxy terminal residue (i.e., the free carboxy group at the C-terminal end of the peptide) of the peptide or peptidomimetic (or salt thereof) is modified (e.g., for protection against degradation). In an embodiment, the modification is an amidation (replacement of the OH group by a $NH_2$ group), thus in such a case $Z^2$ is a $NH_2$ group. In a further embodiment, $Z^2$ is a sequence of one or more amino acids (e.g., 1 to 25 additional amino acids, for example 20, 19, 18, 17, 16, 15, 14, 13, 12, 11, 10, 9, 8, 7, 6, 5, 4, 3, 2, or 1 amino acids).

In an embodiment, the peptide (or salt thereof) comprises or consists of the following sequence: Ile-Arg-Pro-Gly-Thr-Val-LeU-Arg-Ile-Arg-Gly-Leu-Val-$NH_2$ (SEQ ID NO:3).In another embodiment, the peptide (or salt thereof) comprises or consists of the following sequence: Leu-Asp-Ser-Val-Arg-Ile-Phe-$NH_2$ (SEQ ID NO:1). In another embodiment, the peptide (or salt thereof) comprises or consists of the following sequence: Phe-Glu-Val-Leu-Ile-Ile-Ala-Ser-Asp-Asp-Gly-Phe-Lys-Ala-Val-Val-Gly-$NH_2$ (SEQ ID NO:7). In another embodiment, the peptide (or salt thereof) comprises or consists of the following sequence: Asp-Gly-Phe-Lys-Ala-Val-Val-Gly-Asp-Ala-Gln-Tyr-His-His-$NH_2$ (SEQ ID NO:5).

The peptide or peptidomimetic (or salt thereof) of the present invention may further comprise modifications that confer additional biological properties to the peptide or peptidomimetic such as protease resistance, plasma protein binding, increased plasma half-life, intracellular penetration, etc. Such modifications include, for example, covalent attachment of fatty acids (e.g., $C_6$-$C_{18}$) to the peptide or peptidomimetic, attachment to proteins such as albumin (see, e.g., U.S. Pat. No. 7,268,113); glycosylation, biotinylation or PEGylation (see, e.g., U.S. Pat. Nos. 7,256,258 and 6,528,485). PEGylation may be carried out using an acylation reaction or an alkylation reaction with a reactive polyethylene glycol molecule. Methods for peptide PEGylation are disclosed, for example, in Roberts et al., Chemistry for peptide and protein PEGylation, *Advanced Drug Delivery Reviews*, Volume 64, Supplement, December 2012, Pages 116-127). In an embodiment, the peptide, peptidomimetic or salt thereof is conjugated to a polyethylene glycol (PEG) chain/moiety (i.e. is PEGylated). The term "PEG chain" refers to polymers of ethylene glycol (represented by the general formula $H(OCH_2CH_2)_nOH$, where n is an integer of 2, 3, 4, 5, 6, 7, 8, 9, or more) which are commercially produced with different molecular weights (e.g., about 200-50,000 Da, 500-40,000 Da, 1000-30,000 Da or 2000-10,000 Da). PEGylated peptides/peptidomimetics may be prepared by modifying certain amino acids in the peptide/peptidomimetic with a suitable group-reactive reagent. For example, a Cys side chain may be modified with a thiol-reactive agent, or a Lys side chain may be modified with an amine-reactive agent.

The above description of modification of the peptide or peptidomimetic (or salt thereof) does not limit the scope of the approaches nor the possible modifications that can be engineered.

The peptide of the invention may be produced by expression in a host cell comprising a nucleic acid encoding the peptide (recombinant expression) or by chemical synthesis (e.g., solid-phase peptide synthesis). Peptides can be readily synthesized by manual and automated solid phase procedures well known in the art. Suitable syntheses can be performed for example by utilizing "t-Boc" or "Fmoc" procedures. Techniques and procedures for solid phase synthesis are described in for example *Solid Phase Peptide Synthesis: A Practical Approach*, by E. Atherton and R. C. Sheppard, published by IRL, Oxford University Press, 1989. Alternatively, the peptides may be prepared by way of segment condensation, as described, for example, in Liu et al., *Tetrahedron Lett*. 37: 933-936, 1996; Baca et al., *J. Am. Chem. Soc*. 117: 1881-1887, 1995; Tam et al., Int. *J. Peptide Protein Res*. 45: 209-216, 1995; Schnolzer and Kent, Science 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the peptides are described in Nakagawa et al., *J. Am. Chem. Soc.* 107: 7087-7092, 1985.

Peptides and peptide analogs comprising naturally occurring amino acids encoded by the genetic code may also be prepared using recombinant DNA technology using standard methods. Peptides produced by recombinant technology may be modified (e.g., N-terminal acylation [e.g., acetylation], C-terminal amidation), using methods well known in the art. Therefore, in embodiments, in cases where a peptide described herein contains naturally occurring amino acids encoded by the genetic code, the peptide may be produced using recombinant methods, and may in embodiments be subjected to for example the just-noted modifications (e.g., acylation, amidation). Accordingly, in another aspect, the invention further provides a nucleic acid encoding the above-mentioned domain or peptide. The invention also provides a vector comprising the above-mentioned nucleic acid. In yet another aspect, the present invention provides a cell (e.g., a host cell) comprising the above-mentioned nucleic acid and/or vector. The invention further provides a recombinant expression system, vectors and host cells, such as those described above, for the expression/production of a peptide of the invention, using for example culture media, production, isolation and purification methods well known in the art.

The peptide or peptidomimetic (or salt thereof) of the invention can be purified by many techniques of peptide purification well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody that specifically binds the peptide or peptidomimetic may for example be used.

In another aspect, the present invention provides a composition (e.g., a pharmaceutical composition) comprising the above-mentioned agent (e.g., peptide, peptidomimetic or salt thereof). In an embodiment, the composition further comprises one or more pharmaceutically acceptable carriers, excipient, and/or diluents.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e. g., human, animal) without excessive toxicity, irritation, allergic response, or other problem or complication, commensurate with a reasonable benefit/risk ratio.

The term "pharmaceutically acceptable carriers, excipient, and/or diluents" refers to additives commonly used in the preparation of pharmaceutical compositions and includes, for example, solvents, dispersion media, saline solutions, surfactants, solubilizing agents, lubricants, emulsifiers, coatings, antibacterial and antifungal agents, chelating agents, pH-modifiers, soothing agents, buffers, reducing agents, antioxidants, isotonic agents, absorption delaying agents or the like (see, e.g., Rowe et al., *Handbook of Pharmaceutical Excipients*, Pharmaceutical Press; $6^{th}$ edition, 2009).

The agent that inhibits prototypic galectin (e.g., galectin-7) dimerization (e.g., peptide, peptidomimetic or salt thereof) of the present invention may be formulated for administration via any conventional route, such as intravenous, oral, transdermal, intraperitoneal, subcutaneous, mucosal, intramuscular, intranasal, intrapulmonary, parenteral or topical administration. The preparation of such formulations is well known in the art (see, e.g., *Remington: The Science and Practice of Pharmacy*, Lippincott Williams & Wilkins; $21^{st}$ edition, 2005).

The agent that inhibits prototypic galectin (e.g., galectin-7) dimerization (e.g., peptide, peptidomimetic or salt thereof) may be used to inhibit any biological, physiological and/or pathological process that involves a prototypic galectin (e.g., galectin-7) homodimerization or any biological process that involves a prototypic galectin (e.g., galectin-7) heterodimerization with other proteins, such as members of the Bcl-2 family (reference [15]).

In another aspect, the present invention provides a method (in vitro or in vivo) for inhibiting the dimerization of a prototypic galectin (e.g., galectin-7), said method comprising contacting said prototypic galectin (e.g., galectin-7) with the agent that inhibits a prototypic galectin (e.g., galectin-7) dimerization (e.g., peptide, peptidomimetic or salt thereof) or the composition described herein. In an embodiment, the above-mentioned method is for inhibiting the dimerization of a prototypic galectin (e.g., galectin-7) in a cell or in the extracellular space (since prototypic galectins such as galectin-7 are released by cells via a non-classical secretory pathway). The present invention also provides the use of the agent that inhibits a prototypic galectin (e.g., galectin-7) dimerization (e.g., peptide, peptidomimetic or salt thereof) or the composition described herein for inhibiting the dimerization of a prototypic galectin (e.g., galectin-7). The present invention also provides the use of the agent that inhibits a prototypic galectin (e.g., galectin-7) dimerization (e.g., peptide, peptidomimetic or salt thereof) or the composition described herein for the manufacture of a medicament for inhibiting the dimerization of a prototypic galectin (e.g., galectin-7).

Recombinant human galectin-7 has been shown to kill certain types of cells, such as Jurkat T cells, monocytes and human peripheral T cells ([39] and Example 3 below), suggesting that galectin-7 has immunosuppressive properties. In another aspect, the present invention provides a method for inhibiting galectin-7-mediated apoptosis in a cell, said method comprising contacting said cell with the agent that inhibits galectin-7 dimerization (e.g., peptide, peptidomimetic or salt thereof) or the composition described herein. The present invention also provides the use of the agent that inhibits galectin-7 dimerization (e.g., peptide, peptidomimetic or salt thereof) or the composition described herein for inhibiting galectin-7-mediated apoptosis in a cell. The present invention also provides the use of the agent that inhibits galectin-7 dimerization (e.g., peptide, peptidomimetic or salt thereof) or the composition described herein for the manufacture of a medicament for inhibiting galectin-7-mediated apoptosis in a cell. In an embodiment, the above-mentioned cell is an immune cell, such as a T lymphocyte or a monocyte. In another aspect, the present invention provides a method for inhibiting galectin-7-mediated immunosuppression in a subject, said method comprising administering to said subject an effective amount of the agent that inhibits galectin-7 dimerization (e.g., peptide, peptidomimetic or salt thereof) or the composition described herein. The present invention also provides the use of the agent that inhibits galectin-7 dimerization (e.g., peptide, peptidomimetic or salt thereof) or the composition described herein for inhibiting galectin-7-mediated immunosuppression in a subject. The present invention also provides the use of the agent that inhibits galectin-7 dimerization (e.g., peptide, peptidomimetic or salt thereof) or the composition described herein for the manufacture of a medicament for inhibiting galectin-7-mediated immunosuppression in a subject. In an embodiment, the subject suffers from a galectin-7-expressing cancer.

In another aspect, the present invention provides a method for treating a prototypic galectin- (e.g., galectin-7) expressing cancer (e.g., inhibiting tumor growth and/or metastasis) in a subject, said method comprising administering to said subject an effective amount of the agent that inhibits prototypic galectin (e.g., galectin-7) dimerization (e.g., peptide, peptidomimetic or salt thereof) or the composition described herein. The present invention also provides the use of the agent that inhibits prototypic galectin- (e.g., galectin-7) dimerization (e.g., peptide, peptidomimetic or salt thereof) or the composition described herein for treating a prototypic galectin- (e.g., galectin-7) expressing cancer in a subject. The present invention also provides the use of the agent that inhibits prototypic galectin (e.g., galectin-7) dimerization (e.g., peptide, peptidomimetic or salt thereof) or the composition described herein for the manufacture of a medicament for treating a prototypic galectin- (e.g., galectin-7) expressing cancer in a subject. In an embodiment, the prototypic galectin- (e.g., galectin-7) expressing cancer is of epithelial origin. In another embodiment, the prototypic galectin- (e.g., galectin-7) expressing cancer is a breast cancer, an ovarian cancer or a lymphoma. In a further embodiment, the prototypic galectin- (e.g., galectin-7) expressing cancer is a breast cancer. In another embodiment, the prototypic galectin- (e.g., galectin-7) expressing cancer is an ovarian cancer. In another embodiment, the prototypic galectin- (e.g., galectin-7) expressing cancer is a lymphoma. In another embodiment, the cancer is a cancer of neural cells, for example a medulloblastoma.

In another embodiment, the agent that inhibits prototypic galectin (e.g., galectin-7) dimerization could be used to treat other diseases where prototypic galectins (e.g., galectin-7) are involved, for example infectious diseases or diseases/injury of the skin, where galectin-7 is normally expressed (Gendronneau et al., *Mol Biol Cell.* 2008 December; 19(12): 5541-9; Gendronneau et al., *PLoS One.* 2015 Mar. 5; 10(3): e0119031), in graft rejection (Luo et al., *Transplant Proc.* 2013 March; 45(2):630-4), asthma (Yin et al., *Zhonghua Er Ke Za Zhi.* 2006 July; 44(7):523-6), as well as preeclampsia and miscarriage (Menkhorst et al., *Placenta.* 2014 April; 35(4):281-5 and *Placenta.* 2014 March; 35(3):195-201).

The amount of the agent that inhibits agent that inhibits prototypic galectin (e.g., galectin-7) dimerization (e.g., peptide, peptidomimetic or salt thereof) which is effective for the above-noted activities/therapeutic uses will depend on several factors including the nature and severity of the disease, the chosen prophylactic/therapeutic regimen, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect/induce a beneficial prophylactic and/or therapeutic response in the patient over time (in the case of a cancer, a decrease in tumor size, inhibition of tumor cell proliferation, increased survival time, etc.). The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

In an embodiment, the above-mentioned treatment comprises the use/administration of more than one (i.e. a combination of) active/therapeutic agent, including the above-mentioned agent that inhibits prototypic galectin (e.g., galectin-7) dimerization. The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) is used/administered in combination with one or more agent(s) or treatment currently used to prevent or treat the disorder in question (e.g., agents or treatments currently used in the treatment of cancers, such as radiotherapy, surgery and/or targeted therapy).

The present inventors have determined that agents that targets specific domains/residues of galectin-7 that are involved in galectin-7 dimerization, more specifically residues 13-25, 86-102, 95-108, and/or 129-135 of human galectin-7, may be useful to inhibit biological, physiological and/or pathological processes that involves galectin-7 dimerization.

Accordingly, in another aspect, the present invention provides a method for determining whether a test agent that may be used to inhibit a biological, physiological and/or pathological process that involves prototypic galectin (e.g., galectin-7) dimerization, said method comprising: contacting a prototypic galectin (e.g., galectin-7) polypeptide with said test agent; and determining whether said test agent binds to a domain corresponding to residues 13-25, 85-102, 95-108, and/or 129-135 of said prototypic galectin (e.g., galectin-7) polypeptide, wherein the binding of said test agent binds to said domain is indicative that said test agent may be used to inhibit a biological, physiological and/or pathological process that involves prototypic galectin (e.g., galectin-7) dimerization.

In an embodiment, the above-mentioned method further comprises determining whether the test agent inhibits signaling (e.g., activation of a signaling pathway) or activity induced by prototypic galectin (e.g., galectin-7) dimerization in a cell. In an embodiment, the activity is apoptosis.

Test agents (e.g., drug candidates) that may be screened by the method/system of the invention may be obtained from any number of sources including libraries of synthetic or natural compounds. For example, numerous means are available for random and directed synthesis of a wide variety of organic compounds and biomolecules, including expression of randomized oligonucleotides, peptides, etc. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Screening assay systems may comprise a variety of means to enable and optimize useful assay conditions. Such means may include but are not limited to: suitable buffer solutions, for example, for the control of pH and ionic strength and to provide any necessary components for optimal activity and stability (e.g., protease inhibitors), temperature control means for optimal activity and/or stability of galectin-7, and detection means to enable the detection of the binding of the test agent to galectin-7. A variety of such detection means may be used, including but not limited to one or a combination of the following: radiolabelling, antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/(strept)avidin), and others.

The prototypic galectin (e.g., galectin-7) polypeptide used in the above-noted method may be a full length prototypic galectin (e.g., galectin-7) polypeptide, or a fragment or variant thereof that comprises a domain corresponding to residues 13-25, 85-102, 95-108, and/or 129-135 of galectin-7.

MODE(S) FOR CARRYING OUT THE INVENTION

The present invention is illustrated in further details by the following non-limiting examples.

Example 1: Materials and Methods

Cell Lines and Reagents. The Jurkat cell line was maintained in RPMI 1640 medium. The culture medium was supplemented with 10% [v/v] fetal bovine serum, 2 mmol/L of L-glutamine, 10 mM HEPES buffer, and 1 mM sodium pyruvate. All cell culture products/reagents were purchased from Life Technologies® (Burlington, ON, Canada).

Peptide Synthesis. Peptides were synthesized using standard Fmoc chemistry, as previously described [27]. Briefly, all peptides were assembled using a semi-automatic multi-reactor system. The Rink-amide resin was used as the solid support, and the amino acids of the peptide sequences were introduced under their Fmoc-N-protected form, i.e. 3 eq based on the original substitution of the resin (0.7 mmol·g$^{-1}$). Couplings of the protected amino acids were mediated by (Benzotriazol-1-yloxy)tris(dimethylamino)phosphonium hexafluorophosphate (BOP, 3 eq) and N,N-Diisopropylethylamine (DIPEA, 5 eq) in DMF for 1 h. Coupling efficiency was monitored with the qualitative ninhydrin test. Fmoc removal was achieved with 20% piperidine in DMF for 20 min. In order to obtain a biotin-conjugated peptide, an ε-amino acid (Fmoc-Ahx-OH) linker was first coupled, as described above, to peptidyl resins and then, following the removal of the Fmoc protecting group, a Biotin-NHS derivative (6 eq, AAPPTec) was attached to the peptidyl resins with triethylamine (TEA, 6 eq) in dimethylformamide. Peptides were then deprotected and removed from the resin via an acidolytic treatment with trifluoroacetic acid (TFA) containing 1,2-ethanedithiol (2.5%), phenol (3%) and water (2.5%) for 2 h at room temperature. The diethyl ether-precipitated crude peptides were purified by preparative RP-HPLC performed on a Waters® PrepLC 4000 System with a Waters® 2487 detector set at 220 nm and an XTerra® Prep MS $C_{18}$ column. A linear gradient from eluent A to B with 1% B per 2-min increments (Eluent A=$H_2O$, 0.1% TFA, Eluent B=60% $CH_3CN$/40% $H_2O$, 0.1% TFA) was used for each purification. Collected fractions were then analyzed by matrix-assisted laser desorption/ionization time-of-flight (MALDI-TOF) mass spectrometry (Voyager® DE System from Applied Biosystems®) in linear mode using the α-cyano-4-hydroxycinnamic acid matrix (Carlsbad, Calif., USA) and analytical RP-HPLC with a Phenomenex® Jupiter $C_{18}$ column to ensure their homogeneity. Fractions corresponding to the desired product with purity greater than 98% were pooled and lyophilized.

Production of recombinant hGal-7 and hGal-1. Human Gal-7 cDNA was cloned into pET-22b(+) using NdeI and HindIII restriction enzymes. Human pET-Gal-1 vector was generously donated by Dr. S. Sato (McGill University, QC, Canada). The proteins were produced in E. coli BL21 (DE3) cells at 37° C. Isopropyl β-D-1-thiogalactopyranoside (IPTG) (1 mM) was added to the bacterial culture at $OD_{600\ nm}$=0.6-0.7 and then incubated for 4 h at 37° C. to allow protein production. Bacterial pellets were resuspended in lysis buffer (0.7 mg/mL lysozyme, 10 mM Tris pH 8, 100 mM NaCl, 1 mM EDTA, 1 mM DTT and a protease inhibitor cocktail) and then incubated for 1 h at 37° C. prior to centrifugation for 30 min at 15,000×g (4° C.). The supernatant was then filtered with 500 mL bottle top filter (22 μm) (Corning®, New York, N.Y., USA) and then ran through a lactose-agarose column (Sigma®, St. Louis, Mo., USA). The protein was eluted in 1 mL fractions with 150 mM lactose solution. Purified fractions were analyzed by SDS-PAGE. The hGal-7 was then concentrated and purified using Centrifugal filter units (Amicon® Ultra-15, 10K) (EMD®, Millipore®, Etobicoke, ON) in 20 mM potassium phosphate at pH 7.1. All subsequent experiments with the recombinant proteins were performed in the same buffer solution unless mentioned otherwise. Brilliant Coomassie blue was purchased from BioRad® (Bio-Rad Laboratories®, Mississauga, ON, Canada). The recombinant human Bcl-2 protein fragment was purchased from Abcam® (Abcam®, Cambridge, UK, Cat # ab73696).

Western Blotting. For the apoptosis tests, whole-cell extracts were homogenized and resuspended in RIPA buffer (Thermo Fisher Scientific®, Rockford, Ill., USA) containing protease inhibitors (Roche®, Laval, QC, Canada). Equal amounts of whole-cell extracts (25 μg) were separated on SDS-PAGE and transferred onto nitrocellulose membranes (Bio-Rad Laboratories®). The membranes were first blocked with 5% milk [w/v] in TBS/0.5% Tween® 20 [v/v] for 1 h at room temperature and subsequently blotted overnight in a solution of TBS containing 3% BSA [w/v] and 0.5% Tween 20 [v/v]. The following antibodies were used: a rabbit anti-Poly-(ADP-ribose) polymerase (PARP)-1 (p25) polyclonal antibody (1:5000; Epitomics®, Burlingame, Calif., USA) and a mouse anti-β-actin (1:10000; Sigma-Aldrich®, St-Louis, Mo., USA). Secondary antibodies consisted of horseradish peroxidase-conjugated donkey anti-rabbit (GE Healthcare®, Buckinghamshire, England) and sheep anti-mouse (GE Healthcare®) IgG. Detection was performed using the enhanced chemiluminescence method (GE Healthcare®). For the recombinant protein tests, each peptide was dissolved and maintained in 20 mM potassium phosphate at pH 7.1. The recombinant proteins and peptide dilutions were pre-incubated for 1 h at 4° C. prior to gel migration. The native polyacrylamide gel was made without SDS to allow molecular weight differentiation between the dimer and monomer. The following antibodies were used: a goat anti-Gal-7 antibody (1:10000; R&D Systems®, Minneapolis, Minn., USA), a mouse anti-Gal-1 antibody (1:10000; Proteintech®, Chicago, Ill., USA) and a rabbit anti-Bcl-2 antibody (1:1000; Abcam®, Cambridge, UK). Secondary antibodies consisted of donkey anti-goat (R&D Systems®) or sheep anti-mouse and sheep anti-rabbit (GE Healthcare®) IgG. Detection was performed as described above.

Fluorescent Binding Assay. Recombinant hGal-7 or hGal-1 (10 µg/mL) was coated overnight at 4° C. on black, flat bottom, 96-well polystyrene microplates (Ultident®, Montreal, QC, Canada). Thereafter, the plate was blocked with Reagent diluent (PBS-BSA 1%) for 1 h, then incubated with unlabeled hGal-7$_{(129-135)}$ (cold) for 60 min and finally incubated with biotin-labeled [Ahx$^0$]hGal-7$_{(129-135)}$ for 2h. Lastly, Streptavidin R-phycoerythrin (1/500, Jackson Immunoresearch®, West Grove, Pa., USA) was applied to samples for 30 min. All incubations were performed at room temperature and the washes between incubations were done with 20 mM potassium phosphate buffer pH 7.1. The plate was read by a Tecan® Infinite M1000 PRO microplate reader at excitation and emission wavelengths of 488 nm and 670 nm, respectively.

FITC Conjugation and hGal-7 Binding Assay. To assess hGal-7 binding onto Jurkat T cells, 5 µL of a 1.25 mg/mL fluorescein isothiocyanate (FITC)/DMSO solution was added to 300 µL of 1.7 µg/µL recombinant hGal-7 in a 0.1 M NaHCO$_3$ pH 9.2 solution and incubated for 1 h at room temperature on a roller. FITC-labeled hGal-7 was then purified using a PD-10 Sepharose® column (GE healthcare) and eluted with PBS containing 0.01% [v/v] sodium azide. FITC-labeled hGal-7 (0.1 µM) was then pre-incubated with hGal-7$_{(129-135)}$ (or related peptides) in 20 mM potassium phosphate buffer pH 7.1 for 1 h at 4° C. Jurkat cells (5×10$^5$ cells per sample) were harvested in PBS-0.01% [v/v] sodium azide and incubated for 30 min on ice with the FITC-labeled hGal-7 with and without peptides. Cells were then washed with PBS-0.01% [v/v] sodium azide and resuspended in 400 µL of the same buffer and analyzed on a FACSCalibur® (BD Biosciences®).

Apoptosis Assays with Annexin V/PI Staining. Apoptosis was measured by flow cytometry using FITC-labeled Annexin V (Biolegend®, San Diego, Calif., USA) and propidium iodide. Briefly, the corresponding dilutions of recombinant hGal-7 and hGal-7$_{(123-135)}$ peptides were pre-incubated for 1 h at 4° C. in serum-free RPMI 1640 medium. 2.5×10$^5$ Jurkat cells were then harvested in the same medium and incubated with their corresponding dilutions at 37° C. for 4 h. Cells were washed once in PBS and once in binding buffer (0.01 M HEPES, 0.14 M NaCl, 2.5 mM CaCl$_2$, pH 7.4). Cells were then incubated for 15 min with Annexin V in the dark at room temperature. A total of 400 µL of binding buffer containing 0.25 µg/mL propidium iodide was added to the cells before analysis by flow cytometry.

Statistical analysis. Statistical significance of the experiments was evaluated using the unpaired Student's t-test or the Fisher's exact test. Results were considered statistically significant at $P \leq 0.05$.

Example 2: Development of Peptides that Inhibit hGal-7 Dimerization

Figure 1B:
Figure 2C:
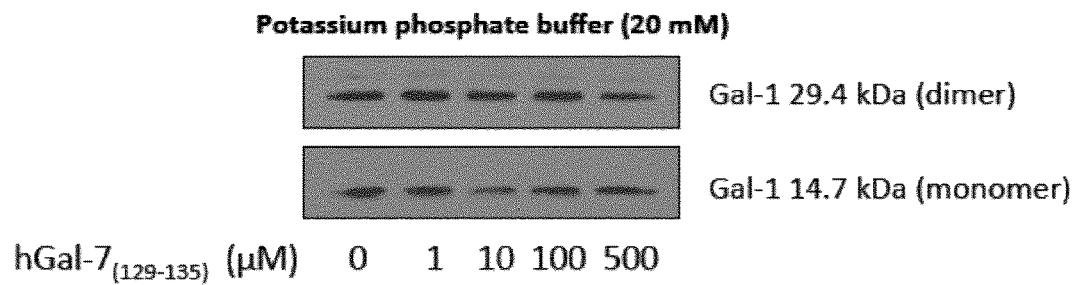
Figure 2D:
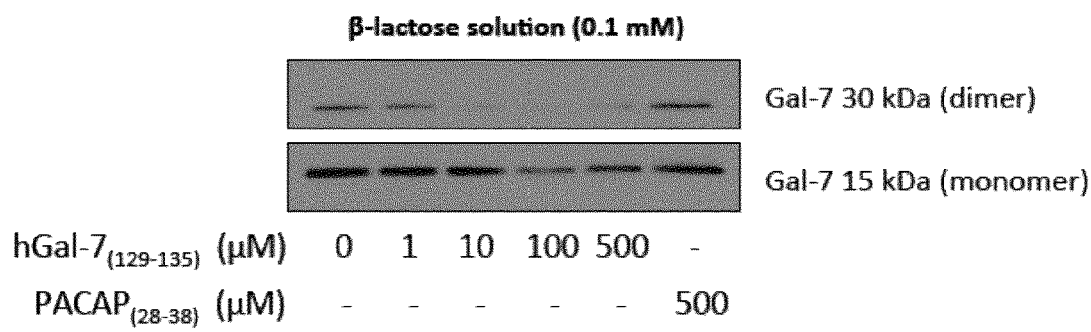
Figure 3:
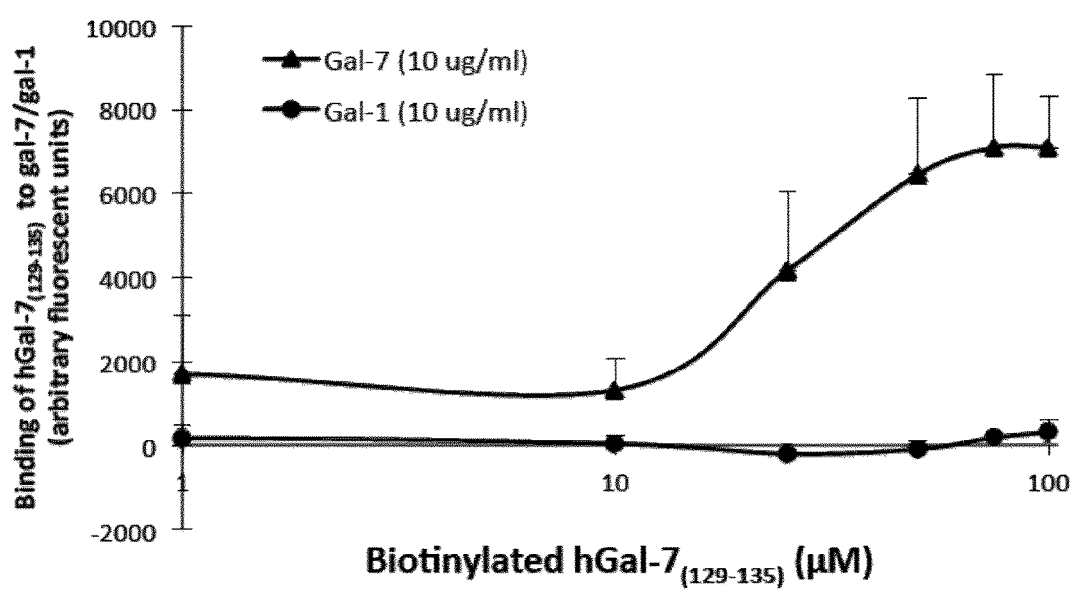
FIG. 3 shows that biotin-labeled hGal-$7_{(129-135)}$ is capable of binding to recombinant hGal-7. Binding curve showing a dose-dependent interaction between biotin-labeled hGal-7$_{(129-135)}$ and hGal-7 or hGal-1. Recombinant hGal-7 or hGal-1 (10 μg/ml) were coated on 96-well plates overnight and then incubated 60 min with unlabeled hGal-7$_{(129-135)}$ (1 mM) to eliminate non-specific binding. Incubation with increasing concentrations of biotin-labeled hGal-7$_{(129-135)}$ was performed for 120 min. Results are representative of three independent experiments. Error bars represent standard deviation.
Figure 6A:
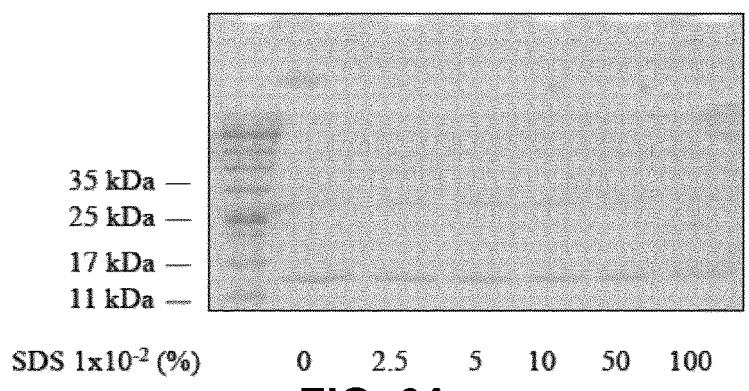
FIGS. 6A to 6C show the visualization of the dimer-monomer equilibrium of hGal-7 in electrophoretic polyacrylamide gel in low SDS conditions. Recombinant hGal-7 (4 μg) was incubated with increasing SDS concentrations (%). hGal-7 was then migrated in a SDS-free gel and 0.1% SDS running buffer for 1h, at 150V (FIG. 6A) and in a SDS-free gel and running buffer for 4 h, at 100V (FIG. 6B).
Figure 6B:
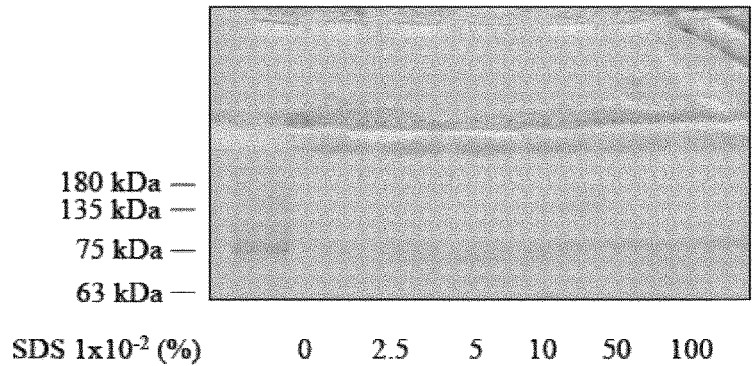
Figure 6C:
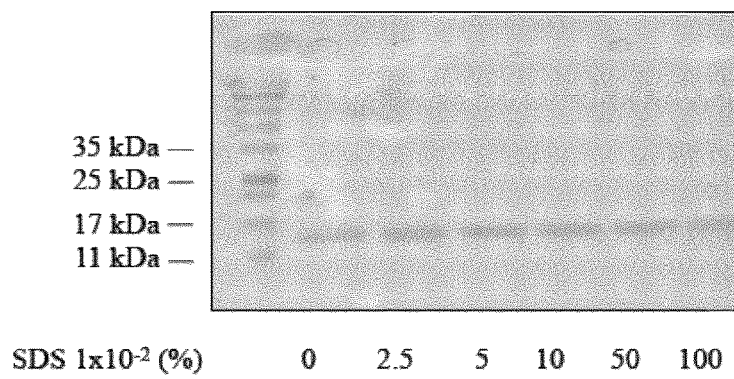
Figure 7A:
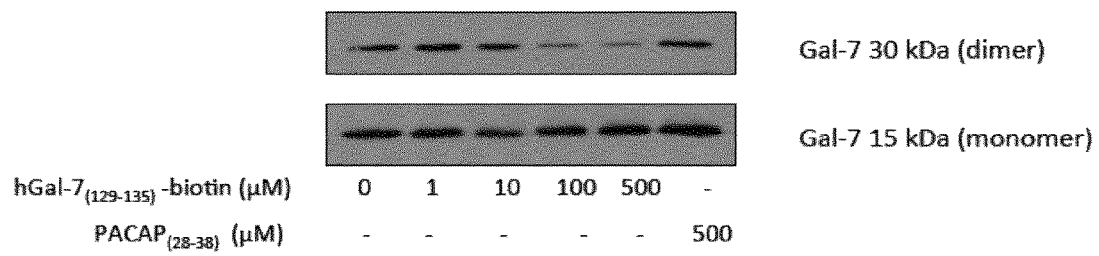
FIGS. 7A and 7B show the disruption of hGal-7 dimer by increasing concentrations of the hGal-7$_{(129-135)}$-biotin peptide.
Figure 7B:
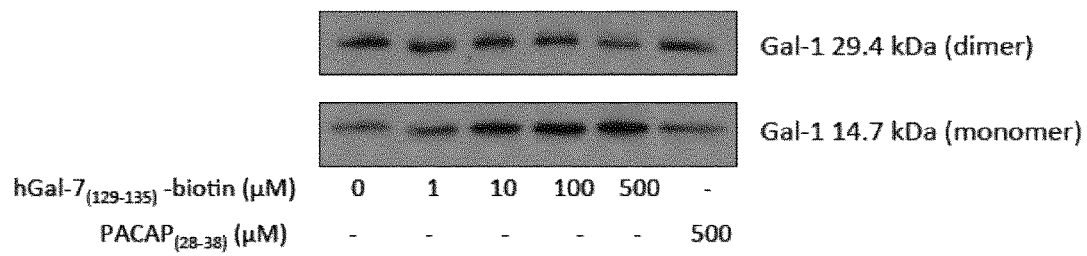
Figure 8A:
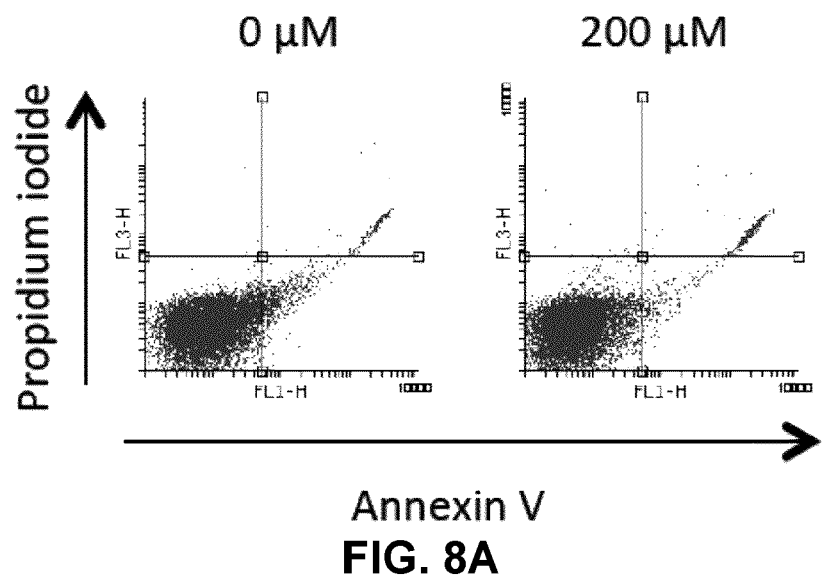
FIGS. 8A to 8D show that peptides hGal-7$_{(129-135)}$ and PACAP$_{28-38}$ do not induce toxicity in Jurkat T cells.
Figure 8B:
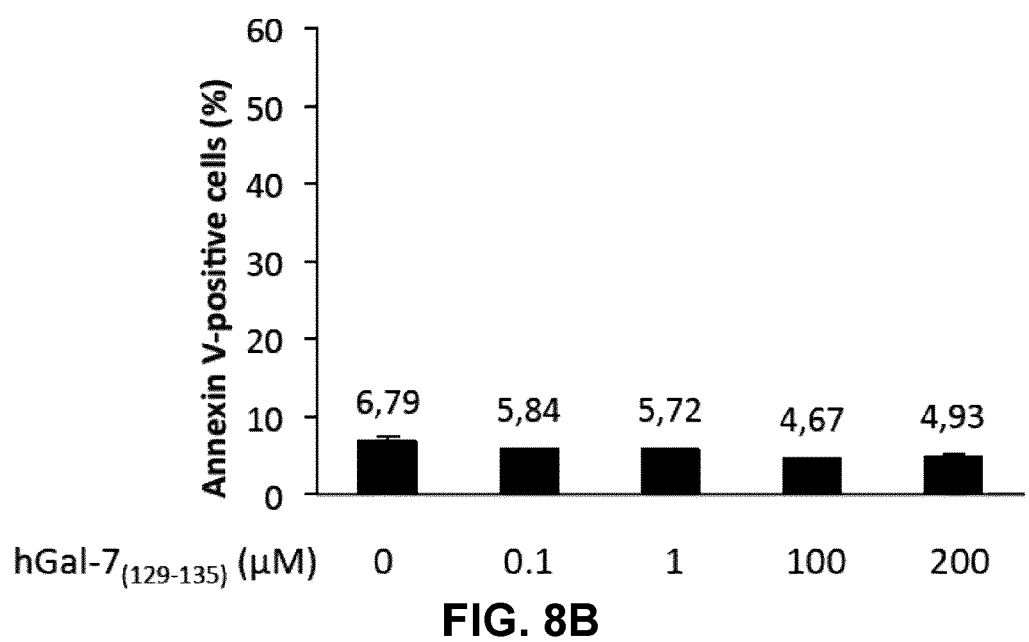
Figure 8C:
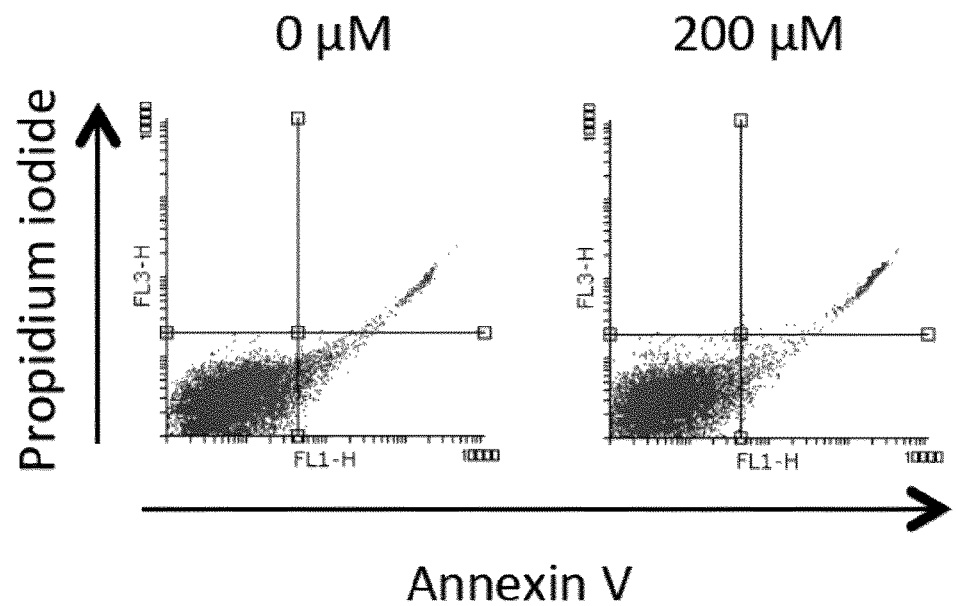
Figure 8D:
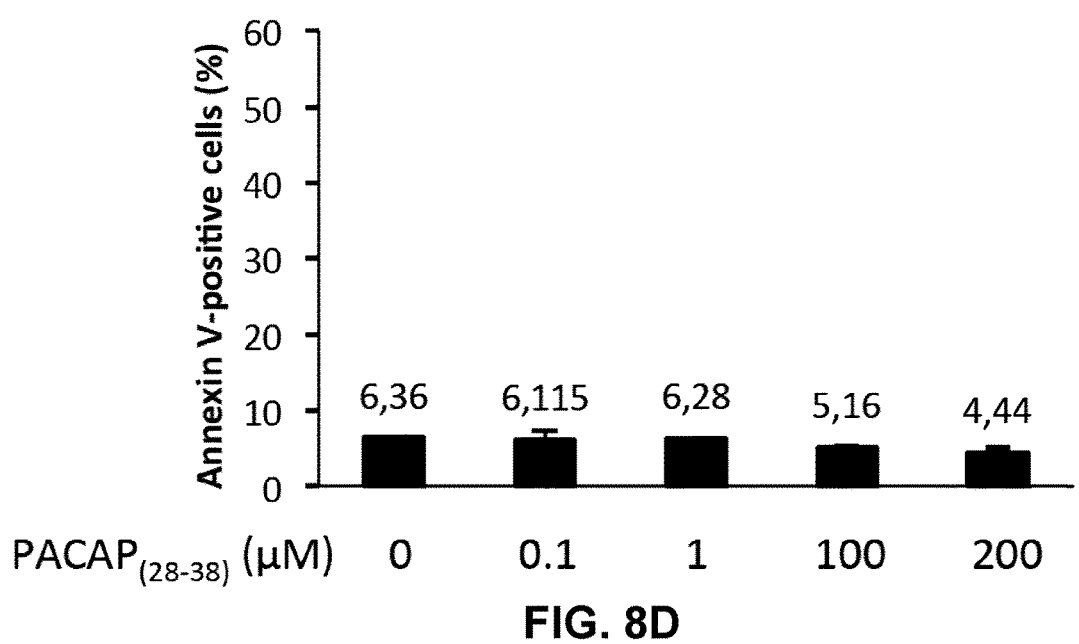
Figure 9A:
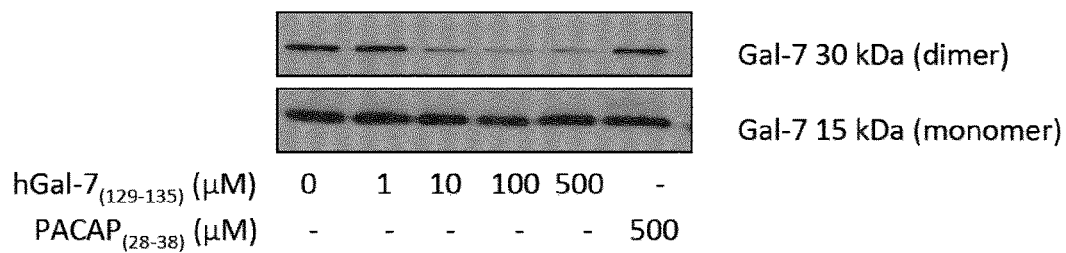
FIGS. 9A to 9E show that Ala-scan mutants of hGal-7$_{(129-135)}$ differ in their ability to disrupt hGal-7 dimer formation. Disruption of hGal-7 dimer was measured in response to increasing concentrations of hGal-7$_{(129-135)}$ (FIG. 9A) and its various Ala-scan mutants: [Ala$^{130}$]hGal-7$_{(129-135)}$ (FIG. 9B); [Ala$^{131}$]hGal-7$_{(129-135)}$ (FIG. 9C); [Ala$^{133}$]hGal-7$_{(129-135)}$ (FIG. 9D); and [Ala$^{135}$]hGal-7$_{(129-135)}$ (FIG. 9E). The recombinant hGal-7 (0.5 μM) was incubated with increasing concentrations of hGal-7$_{(129-135)}$ peptides. The effect on the monomeric and dimeric forms of hGal-7 was assessed by Western blotting in low-SDS conditions. The control peptide PACAP$_{28-38}$ was used in order to ensure the specificity of hGal-7$_{(129-135)}$. Results are representative of three independent experiments.
Figure 9B:
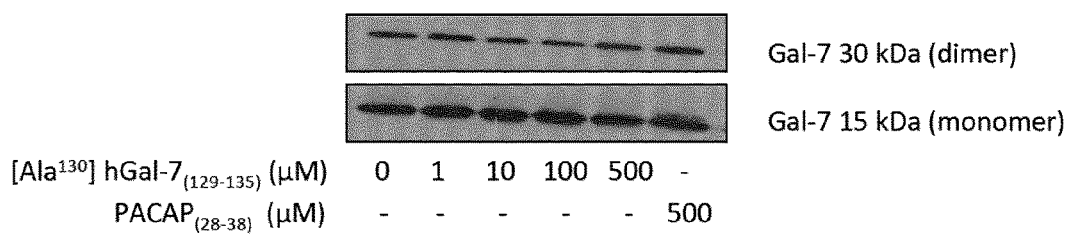
Figure 9C:
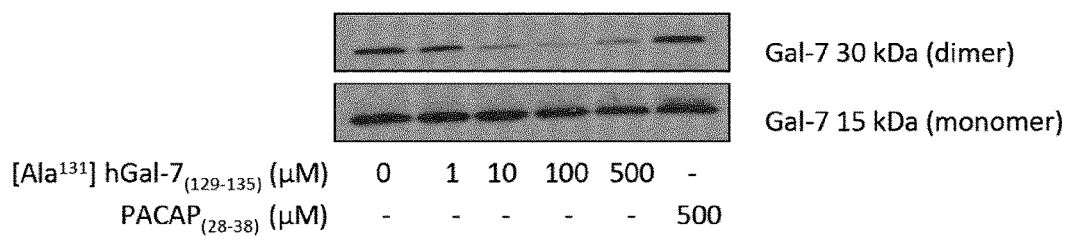
Figure 9D:
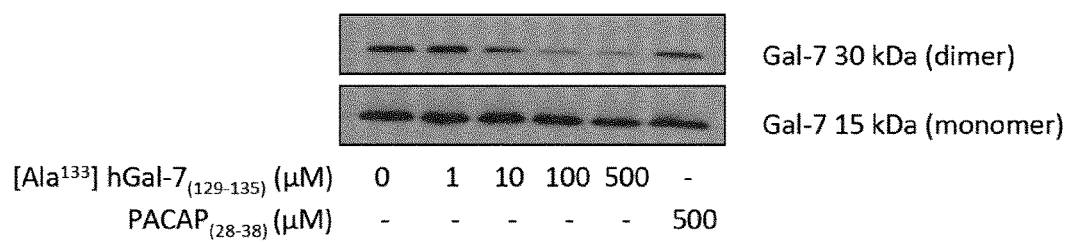
Figure 9E:
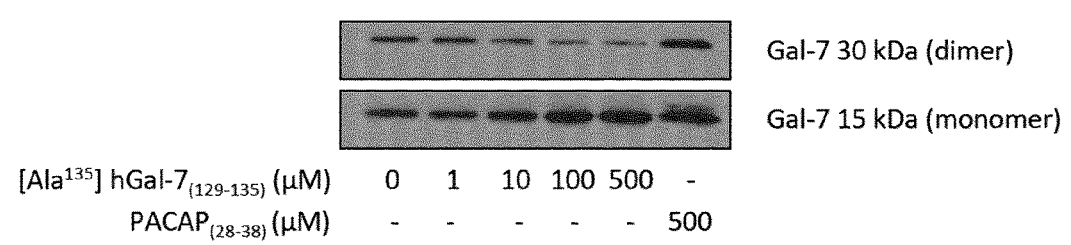

Peptides corresponding to residues 13-25 (hGal-7$_{(13-25)}$; H-Ile-Arg-Pro-Gly-Thr-Val-Leu-Arg-Ile-Arg-Gly-Leu-Val-Nh$_2$ (SEQ ID NO:3)), 85-102 (hGal-7$_{(55-102)}$; H-Phe-Glu-Val-Leu-Ile-Ile-Ala-Ser-Asp-Asp-Gly-Phe-Lys-Ala-Val-Val-Gly-NH$_2$ (SEQ ID NO:7)), 95-108 (hGal-7$_{(95-108)}$; H-Asp-Gly-Phe-Lys-Ala-Val-Val-Gly-Asp-Ala-Gln-Tyr-His-His-NH$_2$ (SEQ ID NO:5)), and 129-135 (hGal-7$_{(129-135)}$; H-Leu-Asp-Ser-Val-Arg-Ile-Phe-NH$_2$ (SEQ ID NO:1)) of hGal-7, were synthesized and tested for their ability to inhibit the dimerization of hGal-7, a prototypic galectin. To determine whether these peptides could inhibit the formation of the hGal-7 homodimer, recombinant hGal-7 (0.5 µM) was incubated with increasing concentrations of hGal-7.sub$_{(13-25)}$, hGal-7$_{(85-102)}$, hGal-7$_{(95-108)}$ or hGal-7$_{(129-135)}$ and the formation of homodimers was measured. To measure the ability of the peptides to disrupt the formation of hGal-7 dimers, a mild denaturing (low SDS) native gel electrophoresis, a commonly used approach to visualize monomer-dimer equilibrium, was used (FIG. 1A and FIG. 6) [32-36]. The results showed a consistent, decrease of hGal-7 homodimers starting at a 10 µM concentration of hGal-7$_{(129-135)}$, with a saturation dose of 100 µM (FIG. 2A). Similar results were obtained with hGal-7$_{(13-25)}$, hGal-7$_{(85-102)}$, or hGal-7$_{(95-108)}$ but these compounds appeared less potent than hGal-7$_{(129-135)}$ to disrupt hGal-7 homodimers (FIG. 2C). No such effect was observed using the control peptide PACAP$_{(28-38)}$, which was selected based on similarity in amino acid length and minimal toxicity on the cell line, (FIG. 2A), or on a recombinant human Gal-1 (hGal-1) (FIG. 2C), hGal-1 was chosen as a galectin selectivity control since it is a prototype galectin and shares the greatest sequence similarity to galectin-7 (38%) [30]. Moreover, the ability of the hGal-7$_{(129-135)}$ peptide to disrupt the formation of hGal-7 homodimers was not inhibited by the presence of lactose (FIG. 2D). Further, the ability of hGal-7$_{(129-135)}$ to bind hGal-7 in a concentration-dependent and specific manner was further confirmed using a solid phase binding assay. In this assay, a biotinylated version of hGal-7$_{(129-135)}$, still capable of specifically inhibiting the formation of hGal-7 homodimers, (FIG. 7) was used to measure binding on immobilized recombinant hGal-7 (FIG. 3). Again, binding was shown to be specific since biotinylated hGal-7$_{(129-135)}$ could bind hGal-7 and not hGal-1. This specificity at disrupting hGal-7 dimer formation is provided by distinct three-dimensional arrangements between otherwise very similar galectin homologues. Indeed, while all monomeric galectins reveal identical topologies, dimer formation in hGal-7 proceeds through a "back-to-back" topology of the monomers and hGal-1 adopts a "side-by-side" structural arrangement (FIG. 1B) [30]. This structural organization provides additional means to specifically target and disrupt galectin function.

Figure 4A:
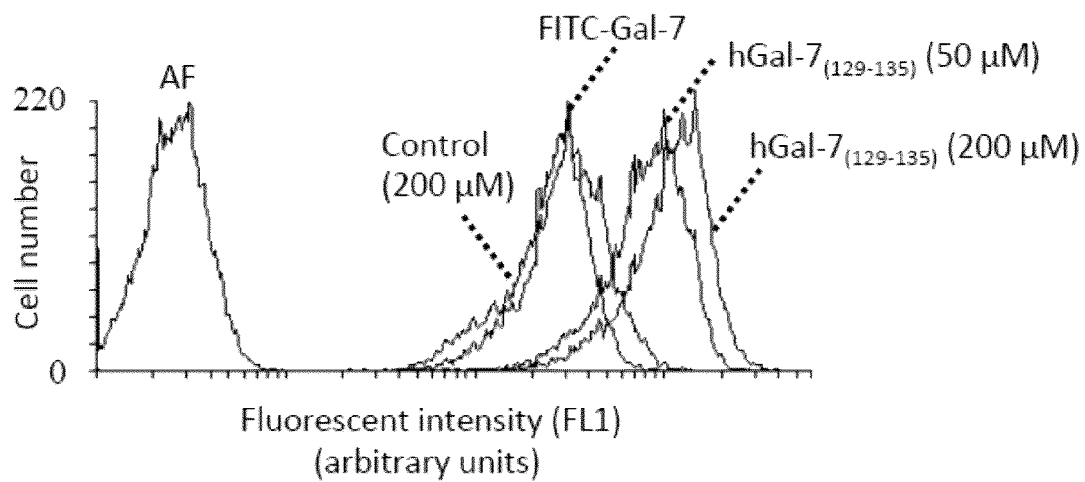
FIGS. 4A and 4B show the increased binding of hGal-7 on Jurkat T cells due to increasing concentrations of hGal-7$_{(129-135)}$.
Figure 4B:
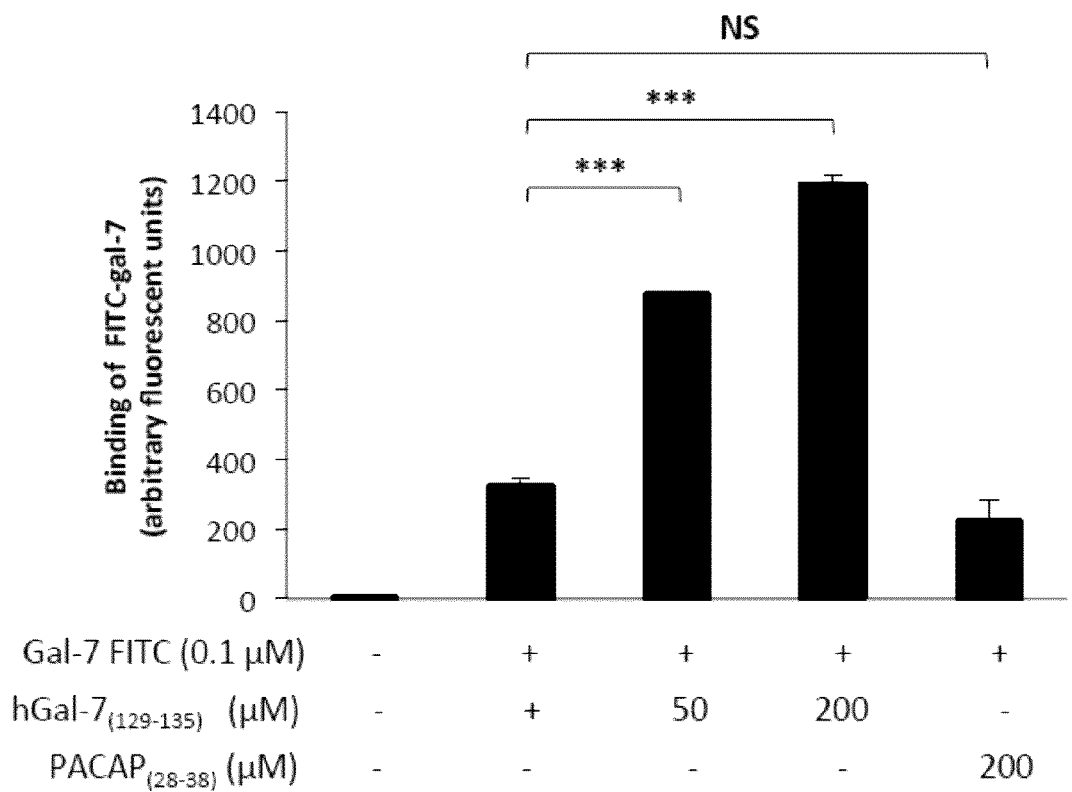
Figure 5A:
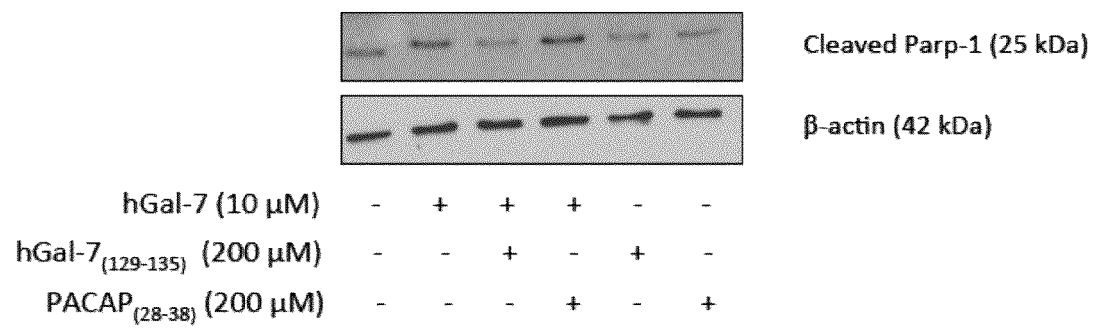
FIGS. 5A to 5C show that the apoptotic levels of Jurkat T cells induced by hGal-7 were decreased due to the presence of hGal-7$_{(129-135)}$.
Figure 5B:
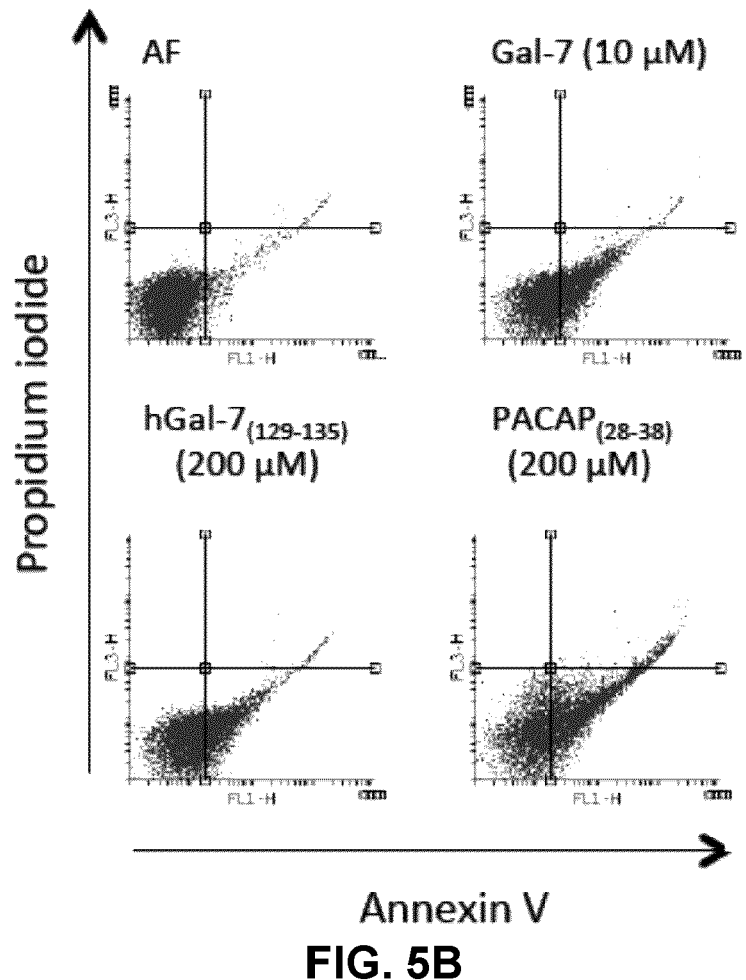
Figure 5C:
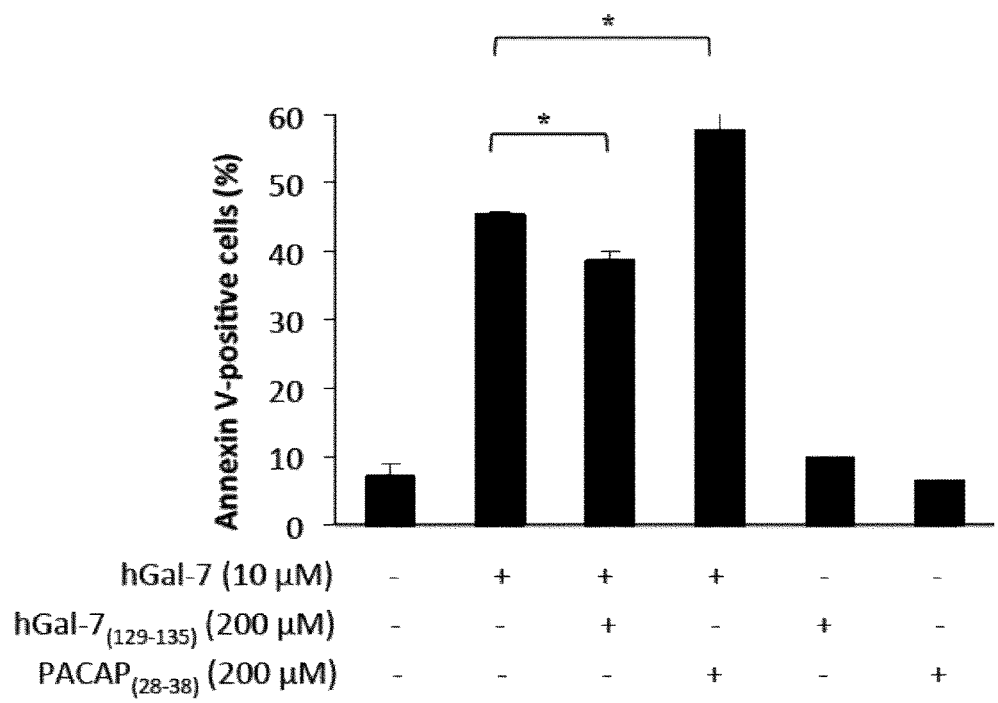

Example 3: hGal-7$_{(129-135)}$ Modulates the Binding of hGal-7 on Jurkat T Cells Galectins are well known for their ability to bind glycosylated cell surface receptors, most notably on Jurkat T cells, on which galectin binding induces apoptosis [37-43]. It was thus tested whether hGal-7$_{(129-135)}$ could modulate the binding of hGal-7 on Jurkat T cells, a cell model that is commonly used to test the pro-apoptotic activity of galectins [44-46]. For this purpose, recombinant hGal-7 was labeled with fluorescein isothiocyante (FITC) and its binding on the surface of Jurkat T cells was measured by flow cytometry in absence or presence of increasing concentrations of hGal-7$_{(129-135)}$. The results showed that hGal-7$_{(129-135)}$ increased the fluorescent intensity of Jurkat T cells in a concentration-dependent manner following incubation with equal amounts (0.1 µM) of FITC-labeled hGal-7, as compared to fluorescence measured in absence of peptide (FIG. 4A). No such effect was observed in presence of a high concentration of the control peptide (PACAP$_{(28-38)}$). The effect of hGal-7$_{(129-135)}$ was specific, statistically significant (FIG. 4B), and consistent with the increased number of monomers, which bind to surface glycosylated receptors through their CRDs [39]. The hGal-7$_{(129-135)}$ peptide also inhibited the ability of hGal-7 to induce apoptosis in Jurkat T cells, as measured by PARP-1 cleavage (FIG. 5A). No such effect was observed with the control peptide. This effect on apoptosis was confirmed by flow cytometry using Annexin V/PI staining (FIGS. 5B and 5C). Incubation of hGal-7$_{(129-135)}$ (or PACAP$_{(28-38)}$) alone did not induce apoptosis in Jurkat T cells (FIG. 8).

Example 4: Alanine Scan of hGal 7$_{(129-135)}$

Figure 1C:
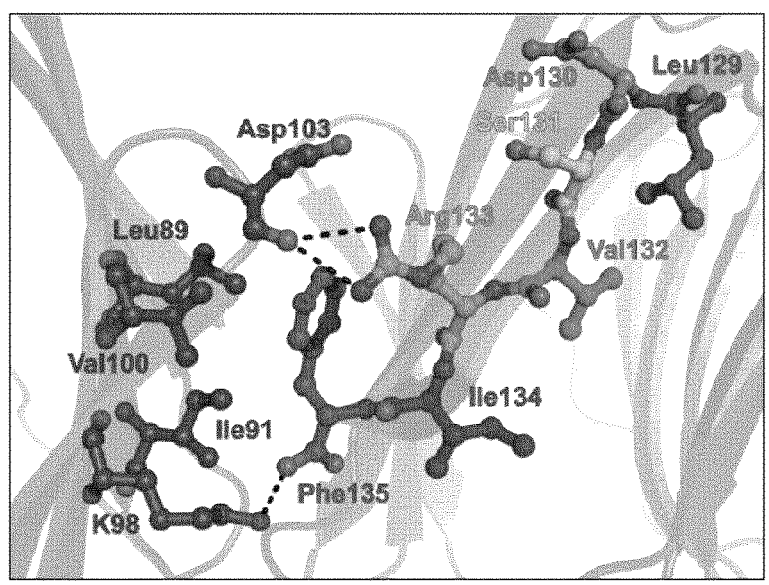

To better understand the interaction between hGal-7$_{(129-135)}$ and hGal-7. The data obtained using an alanine scan strategy has shown that the substitution of the Asp$^{130}$ residue by an Ala moiety abrogates the ability of the peptide to disrupt hGal-7 homodimers (Table I and FIG. 9). Despite the fact that Asp$^{130}$ does not appear to participate in the formation or stabilization of the wild-type hGal-7 dimer interface (FIG. 1C), its replacement to alanine clearly shows significant alteration of the hGal-7$_{(129-135)}$ potency (FIG. 9). These results suggest a distinct binding mode between hGal-7$_{(129-135)}$ and monomeric hGal-7.

TABLE I

Overview of hGal-7$_{(129-135)}$ alanine substitute peptides

| Peptide name | Sequence | Theoretical MW (g/mol) | Actual MW (g/mol) |
|---|---|---|---|
| hGal-7$_{(129-135)}$ | L-D-S-V-R-I-F-NH$_2$ (SEQ ID NO: 2) | 849 | 850.56 |
| [Ala$^{130}$]hGal-7$_{(129-135)}$ | L-A-S-V-R-I-F-NH$_2$ (SEQ ID NO: 9) | 805.10 | 805.01 |
| [Ala$^{131}$]hGal-7$_{(129-135)}$ | L-D-A-V-R-I-F-NH$_2$ (SEQ ID NO: 10) | 833.02 | 833.11 |
| [Ala$^{133}$]hGal-7$_{(129-135)}$ | L-D-S-V-A-I-F-NH$_2$ (SEQ ID NO: 11) | 772.92 | 772.27 |
| [Ala$^{135}$]hGal-7$_{(129-135)}$ | L-D-S-V-R-I-A-NH$_2$ (SEQ ID NO: 12) | 763.90 | 785.61 |

Moreover, the modulation of hGal-7 binding on the surface of Jurkat T cells and an apoptotic response were observed in the presence of the hGal-7$_{(129-135)}$ peptide. The increase in fluorescence was the manifestation of the increased hGal-7 binding on cell surface rather than its accumulation inside the cell, since the binding assays were performed at 0° C. and in the presence of sodium azide (NaN$_3$), which would limit protein internalization [48, 49]. Additionally, the increase of hGal-7 cell surface binding, seen in the presence of hGal-7$_{(129-135)}$, is specific since the control peptide, PACAP$_{(28-38)}$, did not display such effects. Interestingly, even though an increase of cell surface hGal-7 binding was observed, a reduction in the ability of the protein to induce apoptosis of T cells was observed. This supports the idea that the increase in hGal-7 binding on cell surface is due to the increased access of the monomer's CRDs binding glycosylated residues on cell surface receptors while lacking intracellular signaling, highlighting that effective crosslinking of cell surface receptors is involved in the induction of apoptosis [25, 50].

Figure 12A:
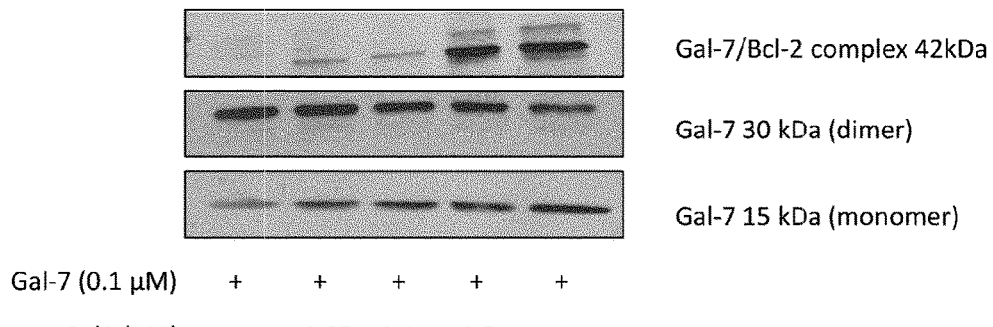
FIGS. 12A to 12C show the dose-dependent disruption of the hGal-7/Bcl-2 heterodimer in the presence of the hGal-7$_{(129-135)}$ peptide.
Figure 12B:
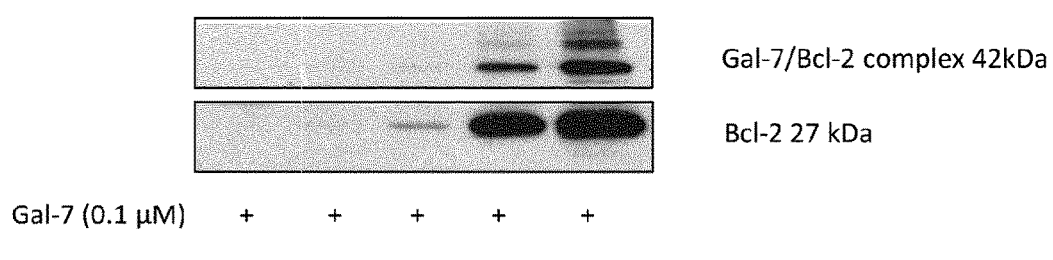
Figure 12C:
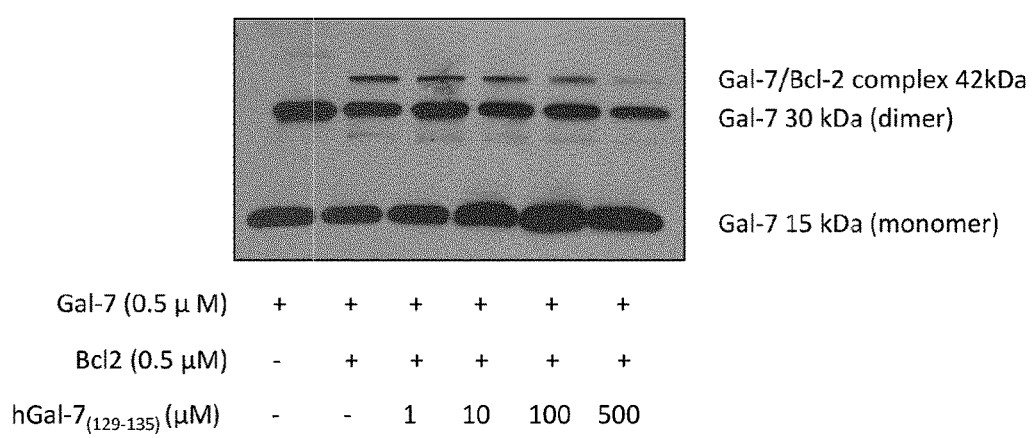

Example 5: hGal-7$_{(129-135)}$ Modulates the Interaction Between hGal-7 and Bcl-2 hGal-7$_{(129-135)}$ was tested for its ability to disrupt the interaction between hGal-7 and Bcl-2 [15]. As shown in FIG. 12C, the amount of hGal-7/Bcl-2 heterodimers was decreased in the presence of hGal-7$_{(129-135)}$, especially at the highest dose of 500 µM. These results provide evidence that the hGal-7$_{(129-135)}$ interferes not only with the homodimerization of hGal-7, but also with its heterodimerization with Bcl-2.

Although the present invention has been described hereinabove by way of specific embodiments thereof, it can be modified, without departing from the spirit and nature of the subject invention as defined in the appended claims. The scope of the claims should not be limited by the preferred embodiments set forth in the examples, but should be given the broadest interpretation consistent with the description as a whole.

REFERENCES

1. Hanahan, D. and R. A. Weinberg, *Hallmarks of cancer: the next generation*. Cell, 2011. 144(5): p. 646-74.
2. Klemm, F. and J. A. Joyce, *Microenvironmental regulation of therapeutic response in cancer*. Trends Cell Biol, 2015. 25(4): p. 198-213.
3. Quail, D. F. and J. A. Joyce, *Microenvironmental regulation of tumor progression and metastasis*. Nat Med, 2013. 19(11): p. 1423-37.
4. Wang, D. and R. N. Dubois, *Eicosanoids and cancer*. Nat Rev Cancer, 2010. 10(3): p. 181-93.
5. Barondes, S. H., et al., *Galectins: a family of animal beta-galactoside-binding lectins*. Cell, 1994. 76(4): p. 597-8.
6. Liu, F. T. and G. A. Rabinovich, *Galectins as modulators of tumour progression*. Nat Rev Cancer, 2005. 5(1): p. 29-41.
7. Vasta, G. R., *Roles of galectins in infection*. Nat Rev Microbiol, 2009. 7(6): p. 424-38.
8. Wang, W., et al., *Tumor-released Galectin-3, a soluble inhibitory ligand of human NKp30, plays an important role in tumor escape from NK cell attack*. J Biol Chem, 2014. 289(48): p. 33311-9.
9. Stannard, K. A., et al., *Galectin inhibitory disaccharides promote tumour immunity in a breast cancer model*. Cancer Lett, 2010. 299(2): p. 95-110.
10. Yang, R. Y., G. A. Rabinovich, and F. T. Liu, *Galectins: structure, function and therapeutic potential*. Expert Rev Mol Med, 2008. 10: p. e17.

11. Inohara, H. and A. Raz, *Effects of natural complex carbohydrate (citrus pectin) on murine melanoma cell properties related to galectin-3 functions.* Glycoconj J, 1994. 11(6): p. 527-32.

12. Pienta, K. J., et al., *Inhibition of spontaneous metastasis in a rat prostate cancer model by oral administration of modified citrus pectin.* J Natl Cancer Inst, 1995. 87(5): p. 348-53.

13. Nangia-Makker, P., et al., *Inhibition of human cancer cell growth and metastasis in nude mice by oral intake of modified citrus pectin.* J Natl Cancer Inst, 2002. 94(24): p. 1854-62.

14. Dings, R. P., et al., *Antitumor agent calixarene 0118 targets human galectin-1 as an allosteric inhibitor of carbohydrate binding.* J Med Chem, 2012. 55(11): p. 5121-9.

15. Villeneuve, C., et al., *Mitochondrial proteomic approach reveals galectin-7 as a novel BCL-2 binding protein in human cells.* Mol Biol Cell, 2011. 22(7): p. 999-1013.

16. Paz, A., et al., *Galectin-1 binds oncogenic H-Ras to mediate Ras membrane anchorage and cell transformation.* Oncogene, 2001. 20(51): p. 7486-93.

17. Akahani, S., et al., *Galectin-3: a novel antiapoptotic molecule with a functional BH1 (NWGR) domain of Bcl-2 family.* Cancer Res, 1997. 57(23): p. 5272-6.

18. Shimura, T., et al., *Implication of galectin-3 in Wnt signaling.* Cancer Res, 2005. 65(9): p. 3535-7.

19. Cooper, D. N., *Galectinomics: finding themes in complexity.* Biochim Biophys Acta, 2002. 1572(2-3): p. 209-31.

20. Fink, N. E., *[Soluble beta-galactoside-binding lectins].* Acta Physiol Pharmacol Ther Latinoam, 1996. 46(1): p. 1-10.

21. Barondes, S. H., et al., *Galectins. Structure and function of a large family of animal lectins.* J Biol Chem, 1994. 269(33): p. 20807-10.

22. Giudicelli, V., et al., *Is human galectin-1 activity modulated by monomer/dimer equilibrium?* Glycobiology, 1997. 7(3): p. viii-x.

23. Levi, G. and V. I. Teichberg, *Isolation and physicochemical characterization of electrolectin, a beta-D-galactoside binding lectin from the electric organ of Electrophorus electricus.* J Biol Chem, 1981. 256(11): p. 5735-40.

24. Fred Brewer, C., *Binding and cross-linking properties of galectins.* Biochim Biophys Acta, 2002. 1572(2-3): p. 255-62.

25. Rabinovich, G. A., et al., *Functions of cell surface galectin-glycoprotein lattices.* Curr Opin Struct Biol, 2007. 17(5): p. 513-20.

26. Garner, O. B. and L. G. Baum, *Galectin-glycan lattices regulate cell-surface glycoprotein organization and signalling.* Biochem Soc Trans, 2008. 36(Pt 6): p. 1472-7.

27. Brkovic, A., et al., *Functional and binding characterizations of urotensin II-related peptides in human and rat urotensin II-receptor assay.* J Pharmacol Exp Ther, 2003. 306(3): p. 1200-9.

28. Hebert, T. E., et al., *A peptide derived from a beta2-adrenergic receptor transmembrane domain inhibits both receptor dimerization and activation.* J Biol Chem, 1996. 271(27): p. 16384-92.

29. George, S. R., et al., *A transmembrane domain-derived peptide inhibits D1 dopamine receptor function without affecting receptor oligomerization.* J Biol Chem, 1998. 273(46): p. 30244-8.

30. Leonidas, D. D., et al., *Structural basis for the recognition of carbohydrates by human galectin-7.* Biochemistry, 1998. 37(40): p. 13930-40.

31. Ermakova, E., et al., *Lactose binding to human galectin-7 (p53-induced gene 1) induces long-range effects through the protein resulting in increased dimer stability and evidence for positive cooperativity.* Glycobiology, 2013. 23(5): p. 508-23.

32. Jahnel, R., et al., *Biochemical characterization of the vanilloid receptor 1 expressed in a dorsal root ganglia derived cell line.* Eur J Biochem, 2001. 268(21): p. 5489-96.

33. Klodmann, J., D. Lewejohann, and H. P. Braun, *Low-SDS Blue native PAGE.* Proteomics, 2011. 11(9): p. 1834-9.

34. Lin, C. L., Y. T. Huang, and J. D. Richter, *Transient CPEB dimerization and translational control.* RNA, 2012. 18(5): p. 1050-61.

35. Hoang, T., M. D. Smith, and M. Jelokhani-Niaraki, *Expression, folding, and proton transport activity of human uncoupling protein-1 (UCP1) in lipid membranes: evidence for associated functional forms.* J Biol Chem, 2013. 288 (51): p. 36244-58.

36. Giudici, A. M., et al., *Detergent-labile, supramolecular assemblies of KcsA: relative abundance and interactions involved.* Biochim Biophys Acta, 2013. 1828(2): p. 193-200.

37. Ito, K., et al., *Galectin-1 as a potent target for cancer therapy: role in the tumor microenvironment.* Cancer Metastasis Rev, 2012. 31(3-4): p. 763-78.

38. Radosavljevic, G., et al., *The roles of Galectin-3 in autoimmunity and tumor progression.* Immunol Res, 2012. 52(1-2): p. 100-10.

39. Labrie, M., et al., *Expression and functions of galectin-7 in ovarian cancer.* Oncotarget, 2014. 5(17): p. 7705-21.

40. Norambuena, A., et al., *Galectin-8 induces apoptosis in Jurkat T cells by phosphatidic acid-mediated ERK1/2 activation supported by protein kinase A down-regulation.* J Biol Chem, 2009. 284(19): p. 12670-9.

41. Petelenz, T., et al., *[A case of isolated, corrected transposition of great arteries diagnosed with non-invasive techniques].* Pol Tyg Lek, 1991. 46(1-3): p. 39-42.

42. Tribulatti, M. V., et al., *Galectin-8 induces apoptosis in the CD4(high)CD8(high) thymocyte subpopulation.* Glycobiology, 2007. 17(12): p. 1404-12.

43. Fukata, Y., et al., *Direct cytocidal effect of galectin-9 localized on collagen matrices on human immune cell lines.* Biochim Biophys Acta, 2014. 1840(6): p. 1892-901.

44. Perillo, N. L., et al., *Apoptosis of T cells mediated by galectin-1.* Nature, 1995. 378(6558): p. 736-9.

45. Stillman, B. N., et al., *Galectin-3 and galectin-1 bind distinct cell surface glycoprotein receptors to induce T cell death.* J Immunol, 2006. 176(2): p. 778-89.

46. Xue, J., et al., *Regulation of galectin-3-induced apoptosis of Jurkat cells by both O-glycans and N-glycans on CD45.* FEBS Lett, 2013. 587(24): p. 3986-94.

47. Henrick, K., et al., *Evidence for subsites in the galectins involved in sugar binding at the nonreducing end of the central galactose of oligosaccharide ligands: sequence analysis, homology modeling and mutagenesis studies of hamster galectin-3.* Glycobiology, 1998. 8(1): p. 45-57.

48. Oliver, D. B., et al., *Azide-resistant mutants of Escherichia coli alter the SecA protein, an azide-sensitive component of the protein export machinery.* Proc Natl Acad Sci USA, 1990. 87(21): p. 8227-31.

49. Kubak, B. M. and W. W. Yotis, *Staphylococcus aureus adenosine triphosphatase: inhibitor sensitivity and release from membrane.* J Bacteriol, 1981. 146(1): p. 385-90.

50. Boscher, C., J. W. Dennis, and I. R. Nabi, *Glycosylation, galectins and cellular signaling.* Curr Opin Cell Biol, 2011. 23(4): p. 383-92.

51. Doan, N. D., et al., *Design and characterization of novel cell-penetrating peptides from pituitary adenylate cyclase-activating polypeptide.* J Control Release, 2012. 163(2): p. 256-65.

52. Than N G et al., PNAS 106, 9731, 2009.

53. Than N G et al., Trends in Endocrinology and Metabolism 23, 23 2012

What is claimed is:

1. A peptide which is of one of the following sequences: Leu-Asp-Ser-Val-Arg-Ile-Phe-NH₂ (SEQ ID NO:2), Ile-Arg-Pro-Gly-Thr-Val-Leu-Arg-Gly-Leu-Val-NH₂ (SEQ ID NO:4), Asp-Gly-Phe-Lys-Ala-Val-Val-Gly-Asp-Ala-Gln-Tyr-His-His-NH₂ (SEQ ID NO:6) or Phe-Glu-Val-Leu-Ile-Ile-Ala-Ser-Asp-Asp-Gly-Phe-Lys-Ala-Val-Val-Gly-NH₂ (SEQ ID NO:8), or a salt thereof.

2. The peptide or salt thereof of claim 1, which is: Leu-Asp-Ser-Val-Arg-Ile-Phe-NH₂(SEQ ID NO:2).

3. The peptide or salt thereof of claim 1, which Ile-Arg-Pro-Gly-Thr-Val-Arg-Ile-Arg-Gly-Leu-Val-NH₂ (SEQ ID NO:4).

4. The peptide or salt thereof of claim 1, which is: Asp-Gly-Phe-Lys-Ala-Val-Val-Gly-Asp-Ala-Gln-Tyr-His-His-NH₂ (SEQ NO:6).

5. The peptide or salt thereof of claim 1, which is: Phe-Glu-Val-Leu-Ile-Ile-Ala-Ser-Asp-Asp-Gly-Phe-Lys-Ala-Vasl-Val-Gly-NH₂ (SEQ ID NO:8).

6. A method for inhibiting the dimerization of native human galectin-7, said method comprising contacting said native human, galectin-7 with an effective amount of the peptide or salt thereof defined in claim 1.

7. The method of claim 6, wherein the peptide or salt thereof is: Leu-Asp-Ser-Val-Arg-Ile-Phe-NH₂ (SEQ ID NO:2).

8. A method for inhibiting galectin-7-mediated apoptosis in, a cell, said method comprising contacting said cell with an effective amount of the peptide or salt thereof defined in claim 1.

9. The method of claim 8, wherein the peptide or salt thereof is: Leu-Asp-Ser-Val-Arg-Ile-Phe-NH₂ (SEQ ID NO:2).

10. A method for treating a galectin-7-expressing-cancer in a subject, said method comprising administering to said subject an effective amount of the peptide or salt thereof defined in claim 1.

11. The method of claim 10, wherein the peptide or salt thereof is: Leu-Asp-Ser-Val-Arg-Ile-Phe-NH₂ (SEQ ID NO:2).

12. The method of claim 10, wherein said galectin-7-expressing cancer is a breast cancer, an ovarian cancer, or a lymphoma.

13. The method of claim 12, wherein the peptide or salt thereof is: Leu-Asp-Ser-Val-Arg-Ile-Phe-NH₂ (SEQ ID NO:2).

14. The method of claim 12, wherein the galectin-7-expressing cancer is breast cancer.

15. The method of claim 12, wherein the galectin-7-expressing cancer is ovarian cancer.

16. The method of claim 12, wherein the galectin-7-expressing cancer is lymphoma.

17. The method of claim 13, wherein the galectin-7-expressing cancer is breast cancer.

18. The method of claim 13, wherein the galectin-7-expressing cancer is ovarian cancer.

19. The method of claim 13, wherein the galectin-7-expressing cancer is lymphoma.

* * * * *

UNITED STATES PATENT AND TRADEMARK OFFICE
CERTIFICATE OF CORRECTION

| | | |
|---|---|---|
| PATENT NO. | : 10,519,239 B2 | Page 1 of 1 |
| APPLICATION NO. | : 15/576609 | |
| DATED | : December 31, 2019 | |
| INVENTOR(S) | : Chatenet et al. | |

It is certified that error appears in the above-identified patent and that said Letters Patent is hereby corrected as shown below:

In the Specification

Column 2, Line 44: Please correct "$Xaa^{15}$" to read -- $Xaa^{19}$ --

Column 2, Line 48: Please correct "$Xaa^{16}$" to read -- $Xaa^{19}$ --

Column 7, Line 57: Please correct "h-Gal-$7_{(129-135)}$-" to read -- h-Gal-$7_{(129-135)}$- --

Column 20, Line 7: Please correct "LeU" to read -- Leu --

Column 25, Lines 59-60: Please correct "(0.7 mmol·$g^-_1$)." to read -- (0.7 mmol·$g^{-1}$). --

In the Claims

Column 43, Line 36, Claim 1: Please correct "Leu-Arg-Gly-Leu" to read
-- Leu-Arg-Ile-Arg-Gly-Leu --

Column 43, Line 43, Claim 3: Please correct "which Ile" to read -- which is: Ile --

Column 43, Line 44, Claim 3: Please correct "Thr-Val-Arg-Ile" to read -- Thr-Val-Leu-Arg-Ile --

Column 43, Line 51, Claim 5: Please correct "Vasl" to read -- Val --

Column 43, Line 60, Claim 8: Please correct "in, a cell" to read -- in a cell --

Signed and Sealed this
Twelfth Day of May, 2020

Andrei Iancu
*Director of the United States Patent and Trademark Office*